(12) United States Patent
Jiang et al.

(10) Patent No.: US 10,189,967 B2
(45) Date of Patent: Jan. 29, 2019

(54) MACROPOROUS PHOTONIC CRYSTAL MEMBRANE, METHODS OF MAKING, AND METHODS OF USE

(71) Applicant: University of Florida Research Foundation, Inc., Gainesville, FL (US)

(72) Inventors: Peng Jiang, Gainesville, FL (US); Yin Fang, Gainesville, FL (US); Beverly Ge, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 303 days.

(21) Appl. No.: 15/145,910

(22) Filed: May 4, 2016

(65) Prior Publication Data

US 2016/0326334 A1 Nov. 10, 2016

Related U.S. Application Data

(60) Provisional application No. 62/158,566, filed on May 8, 2015.

(51) Int. Cl.
| | |
|---|---|
| *B32B 27/32* | (2006.01) |
| *C08J 9/26* | (2006.01) |
| *G02B 1/00* | (2006.01) |
| *C08J 9/36* | (2006.01) |
| *G01N 21/00* | (2006.01) |
| *G02B 5/26* | (2006.01) |

(52) U.S. Cl.
CPC . *C08J 9/26* (2013.01); *C08J 9/36* (2013.01); *G01N 21/00* (2013.01); *G02B 1/005* (2013.01); *C08J 2201/026* (2013.01); *C08J 2201/0442* (2013.01); *C08J 2205/04* (2013.01); *C08J 2205/044* (2013.01); *C08J 2371/02* (2013.01); *G02B 5/26* (2013.01)

(58) Field of Classification Search
CPC ............. G01N 21/00; G01N 2021/773; G01N 2010/775
See application file for complete search history.

(56) References Cited

U.S. PATENT DOCUMENTS

| | | |
|---|---|---|
| 7,630,589 B2 | 12/2009 | Kilic et al. |
| 7,691,325 B2 | 4/2010 | Chopra et al. |
| 7,889,954 B2 | 2/2011 | Sailor et al. |

(Continued)

OTHER PUBLICATIONS

Kobatake, et al., "Rapid and Reversible Shape Changes of Molecular Crystals on Photoirradiation", vol. 446, Apr. 12, 2007, doi: 10.1038/nature05669, pp. 1-4.

(Continued)

*Primary Examiner* — Prashant J Khatri
*Assistant Examiner* — Zachary M Davis
(74) *Attorney, Agent, or Firm* — Thomas Horstemeyer, LLP

(57) ABSTRACT

In accordance with the purpose(s) of the present disclosure, as embodied and broadly described herein, embodiments of the present disclosure, in one aspect, relate to macroporous photonic crystal membranes, structures including macroporous photonic crystal membranes, devices including macroporous photonic crystal membranes, methods of using macroporous photonic crystal membranes, methods of making macroporous photonic crystal membranes, and the like.

14 Claims, 15 Drawing Sheets

(56) References Cited

U.S. PATENT DOCUMENTS

| | | | |
|---|---|---|---|
| 2010/0155325 A1* | 6/2010 | Zhang | B01D 39/1692 |
| | | | 210/500.21 |
| 2010/0315703 A1* | 12/2010 | Purdy | G02B 1/005 |
| | | | 359/350 |
| 2012/0293802 A1 | 11/2012 | Ozin et al. | |
| 2013/0199995 A1* | 8/2013 | Jiang | B01D 67/0006 |
| | | | 210/500.25 |
| 2014/0106468 A1 | 4/2014 | Boersma | |

OTHER PUBLICATIONS

A. Lendlein, "Shape-Memory Polymers", Advances in Polymer Science 226, Springer, New York, NY 2010, 1-209.
Stober et al., "Controlled Growth of Monodisperse Silica Spheres in the Micron Size Range", Journal of Colloid and Interface Science 1968, 26: 62-69.
Habault et al., "Light-triggered self-healing and shape-memory polymers", Chem. Soc. Rev. 2013, 42: 7244-7256.
Yakacki et al., "Shape-Memory Polymers for Biomedical Applications", Adv. Polym. Sci. 2010, 226: 147-175.
T. Xie, "Recent advances in polymer shape memory", Polymer 2011, 52: 4985-5000.
Lendlein et al., "Shape-Memory Effect"—From temporary shape . . . T>46 °C . . . To permanent shape, Angew. Chem. Int. Ed. 2002, 41: 2034-2057.
Liu et al., "Review of progress in shape-memory polymers", J. Mater. Chem., 2007, 17: 1543-1558.
Meng et al., "A Brief Review of Stimulus-active Polymers Responsive to Thermal, Light, Magnetic, Electric, and Water/Solvent Stimuli", Journal of Intelligent Material Systems and Structures, vol. 21—Jun. 2010: 359-885.
Nguyen et al., "Modeling the Relaxation Mechanisms of Amorphous Shape Memory Polymers", M. L. Chambers, Adv. Mater. 2010, 22: 3411-3423.
Stuart et al., "Emerging applications of stimuli-responsive polymer materials", Nature Materials 2010, 9: 101-113.
C. Yakacki, "Shape-Memory and Shape-Changing Polymers", Polymer Reviews, 2013, 53: 1-5.
Kloxin et al., "Covalent adaptable networks: smart, reconfigurable and responsive network systems", Chem. Soc. Rev. 2013, 42: 7161-7173.
Behl et al., "Multifunctional Shape-Memory Polymers", Adv. Mater. 2010, 22: 3388-3410.
L. Ionov, "3D Microfabrication using Stimuli-Responsive Self-Folding Polymer Films", Polymer Reviews, 2013, 53: 92-107.
Felton et al., Soft Matter "Self-folding with shape memory composites", Soft Matter, 2013, 9, 7688-7694.
Gugliuzza et al., "A review on membrane engineering for innovation in wearable fabrics and protective textiles", Journal of Membrane Science 446(2013): 350-375.
Leng et al., "Shape-Memory Polymers—A Class of Novel Smart Materials", Mrs Bulletin 2009, 34: 848-855, www.mrs.org/bulletin.
Metzger et al., "Mechanical Properties of Mechanical Actuator for Treating Ischemic Stroke", Biomedical Microdevices 2002, 4:2: 89-96.
Small IV, et al., "Laser-activated shape memory polymer intravascular thrombectomy device", Optics Express 2005, 13: 8204-8213.
Tobushi et al., "Thermomechanical properties in a thin film of shape memory polymer of polyurethane series", Smart Mater. Struct. (1996) 5: 483-491.
Lendlein et al., "Biodegradable, Elastic Shape-Memory Polymers for Potential Biomedical Applications", Science 2002, vol. 296: 1673-1676.
Xue et al., "Synthesis and characterization of elastic star shape-memory polymers as self-expandable drug-eluting stents", Journal of Materials Chemistry 2012, 22: 7403-7411.
Yakacki et al., "Unconstrained recovery characterization of shape-memory polymer networks for cardiovascular applications", ScienceDirect, Biomaterials 2007, 28: 2255-2263.

Maitland et al., "Photothermal Properties of Shape Memory Polymer Micro-Actuators for Treating Stroke", Lasers in Surgery and Medicine (2002) 30:1-11.
Leng et al., "Synergic effect of carbon black and short carbon fiber on shape memory polymer actuation by electricity", Journal of Applied Physics 2008, 104: 1-4.
Koerner et al., "Remotely actuated polymer nanocomposites—stress-recovery of carbon-nanotube-filled thermoplastic elastomers", nature materials 2004, 3: 115-120.
Yang et al., "Macroporous photonic crystal-based vapor detectors created by doctor blade coating", Appl. Phys. Lett. 2011, 98: 1-3.
Meng et al., "Various shape memory effects of stimuli-responsive shape memory polymers", Smart Materials and Structures 2013, 22: 1-23.
Mather et al., "Shape Memory Polymer Research", Annu. Rev. Mater. Res. 2009. 39: 445-471.
Heuwers et al., "Shape-Memory Natural Rubber: An Exceptional Material for Strain and Energy Storage", Macromolecular Chemistry and Physics 2013, 214: 912-923.
Heuwers et al., "Stress-Induced Stabilization of Crystals in Shape Memory Natural Rubber", Macromolecular Rapid Communications 2013, 34: 180-184.
Xie et al., "Encoding Localized Strain History Through Wrinkle Based Structural Colors", Advanced Materials 2010, 22: 4390-4394.
Xu et al., "Deformable, Programmable, and Shape-Memorizing Micro-Optics", Advanced Functional Materials 2013, 23: 3299-3306.
Kunzelman et al., "Shape memory polymers with built-in threshold temperature sensors", Journal of Materials Chemistry 2008, 18: 1082-1086.
Lv et al., "Shape-Memory Polymer in Response to Solution", Advanced Engineering Materials 2008, 10, No. 6: 592-595.
Huang et al., "Water-driven programmable polyurethane shape memory polymer. Demonstration and mechanism", Applied Physics Letters 2005, 86: 1-3.
Du et al., "Solvent induced shape recovery of shape memory polymer based on chemically cross-linked poly(vinyl alcohol)", Soft Matter, 2010, 6: 3370-3376.
Gu et al., "Water-triggered shape memory of multiblock thermoplastic polyurethanes (TPUs)", RSC Adv. 2013, 3: 15783-15791.
Quitmann et al., "Environmental Memory of Polymer Networks under Stress", Adv. Mater. 2014, 26: 3441-3444.
Ding et al., "Morphology and Water Vapor Permeability of Temperature-Sensitive Polyurethanes", Journal of Applied Polymer Science, (2008) vol. 107: 4061-4069.
J. D. Joannopoulos, R. D. Meade, J. N. Winn, Photonic Crystals: Molding the Flow of Light, Princeton University Press, 135 pages.
Fenzl et al., "Photonic Crystals for Chemical Sensing and Biosensing", Angewandte Chemie Ed. 2015, 53: 3318-3335.
Hatton et al., "Assembly of large-area, highly ordered, crack-free inverse opal films", PNAS 2010, vol. 107, 23: 10354-10359.
Vlasov et al., "On-chip natural assembly of silicon photonic bandgap crystals", Nature 2001, 414: 289-293.
Weissman et al., "Thermally Switchable Periodicities and Diffraction from Mesoscopically Ordered Materials", Science 1996, 274: 959-960.
Arsenault et al., "From colour fingerprinting to the control of photoluminescence in elastic photonic crystals", nature materials 2006, 5: 179-184.
Aguirre et al., "Tunable Colors in Opals and Inverse Opal Photonic Crystals", Advanced Functional Materials 2010, 20: 2565-2578.
Kang et al., "Broad-wavelength-range chemically tunable block-copolymer photonic gels", Nature Materials 2007, 6: 957-960.
Fudouzi et al., "Colloidal Crystals with Tunable Colors and Their Use as Photonic Papers", Langmuir 2003, 19: 3653-9660.
Ge et al., "Rewritable Photonic Paper with Hygroscopic Salt Solution as Ink", Advanced Materials 2009, 21: 4259-4264.
Jang et al., "Combining Pattern Instability and Shape-Memory Hysteresis for Phononic Switching", Nano Lett. 2009, 9, 5: 2113-2119.

(56) References Cited

OTHER PUBLICATIONS

Takeoka et al., "Polymer Gels that Memorize Structures of Mesoscopically Sized Templates. Dynamic and Optical Nature of Periodic Ordered Mesoporous Chemical Gels", Langmuir 2002, 18: 5977-5980.
Ge et al., "Highly Tunable Superparamagnetic Colloidal Photonic Crystals", Angew. Chem. Int. Ed. 2007, 46: 7428-7431.
Chan et al., "Mechanochromic Photonic Gels", Advanced Materials 2013, 25: 3934-3947.
Pan et al., "Response of inverse-opal hydrogels to alcohols", Journal of Materials Chemistry 2012, 22: 2018-2025.
Burgess et al., "Structural colour in colourimetric sensors and indicators", Journal of Materials Chemistry C 2013, 1: 6075-6086.
Yue et al., "Mechano-actuated ultrafast full-colour switching in layered photonic hydrogels", nature communications 2014: 1-8.
Yue et al., "Lamellar Hydrogels with High Toughness and Ternary Tunable Photonic Stop-Band", Advanced Materials 2013, 25: 3106-3110.
Cui et al., "Inverse Opal Spheres Based on Polyionic Liquids as Functional Microspheres with Tunable Optical Properties and Molecular Recognition Capabilities", Angew. Chem. Int. Ed. 2014, 53: 3844-3848.
Han et al., "Full Color Tunable Photonic Crystal from Crystalline Colloidal Arrays with an Engineered Photonic Stop-Band", Adv. Mater. 2012, 24,: 6438-6444.
Yang et al., "From Metastable Colloidal Crystalline Arrays to Fast Responsive Mechanochromic Photonic Gels: An Organic Gel for Deformation-Based Display Panels", Adv. Funct. Mater. 2014, 24: 3197-3205.
Ye et al., "Invisible Photonic Prints Shown by Deformation", Advanced Functional Materials 2014, 24: 6430-6438.
Asher et al., "Photonic Crystal Carbohydrate Sensors: Low Ionic Strength Sugar Sensing", J. Am. Chem. Soc. 2003, 125: 3322-3329.
Holtz et al., "Polymerized colloidal crystal hydrogel films as intelligent chemical sensing materials", Nature 1997, 389: 329-832.
Schäfer et al., "Reversible Light-, Thermo-, and Mechano-Responsive Elastomeric Polymer Opal Films", Chemistry of Materials 2013, 25: 2309-2318.
Schäfer et al., "Fully Reversible Shape Transition of Soft Spheres in Elastomeric Polymer Opal Films", Langmuir 2013, 29: 11275-11283.
Fang et al., "Reconfigurable photonic crystals enabled by pressure-responsive shape-memory polymers", Nature communications 2015: 1-8.
Velev et al., "Porous silica via colloidal crystallization", Nature 1997, 389: 447-448.
Jiang et al., "Template-Directed Preparation of Macroporous Polymers with Oriented and Crystalline Arrays of Voids", J. Am. Chem. Soc. 1999, 121: 11630-11637.
Jiang et al., "Single-Crystal Colloidal Multilayers of Controlled Thickness", Chem. Mater. 1999, 11: 2132-2140.
Tsai et al., "Retainment of pore connectivity in membranes prepared with vapor-induced phase separation", Journal of Membrane Science 2010, 362: 360-373.
Mason et al., "Correlation between bulk morphology and luminescence in porous silicon investigated by pore collapse resulting from drying", Thin Solid Films 2002, 406: 151-158.
Bertone et al., "Thickness Dependence of the Optical Properties of Ordered Silica-Air and Air-Polymer Photonic Crystals", Physical Review Letters 1999, 83, 2: 300-303.
Gemici et al., "Targeted Functionalization of Nanoparticle Thin Films via Capillary Condensation", Nano Letters 2009, 9, 3: 1064-1070.
Potyrailo et al., "Morpho butterfly wing scales demonstrate highly selective vapour response", Nature photonics 2007, 1: 123-128.

\* cited by examiner

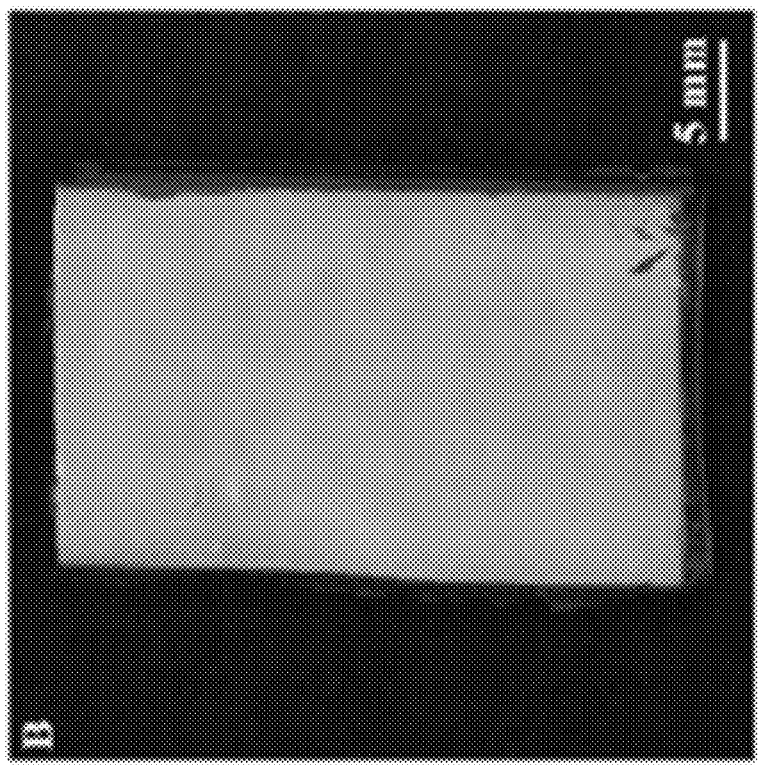
Fig. 1.1B
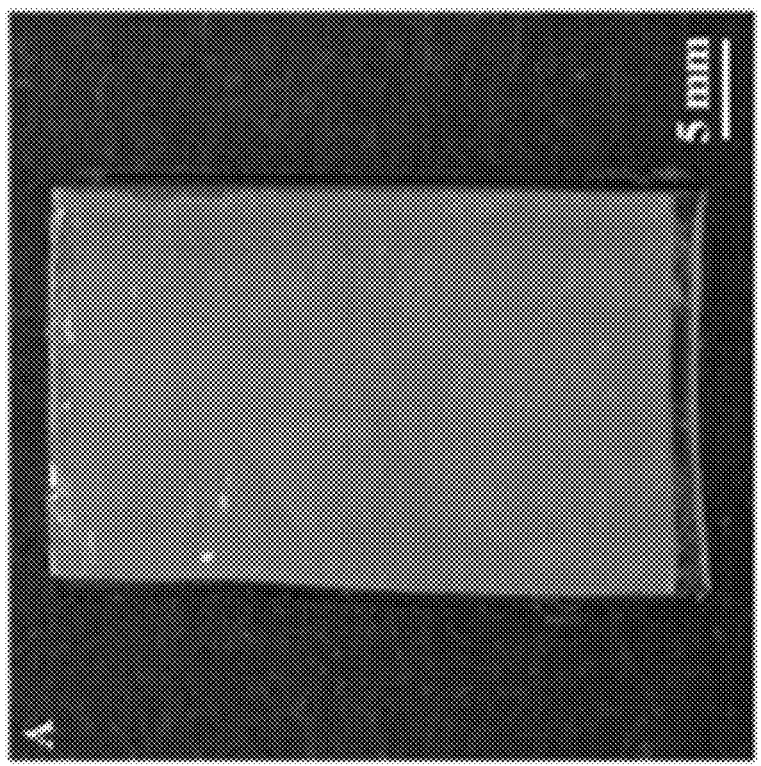
Fig. 1.1A

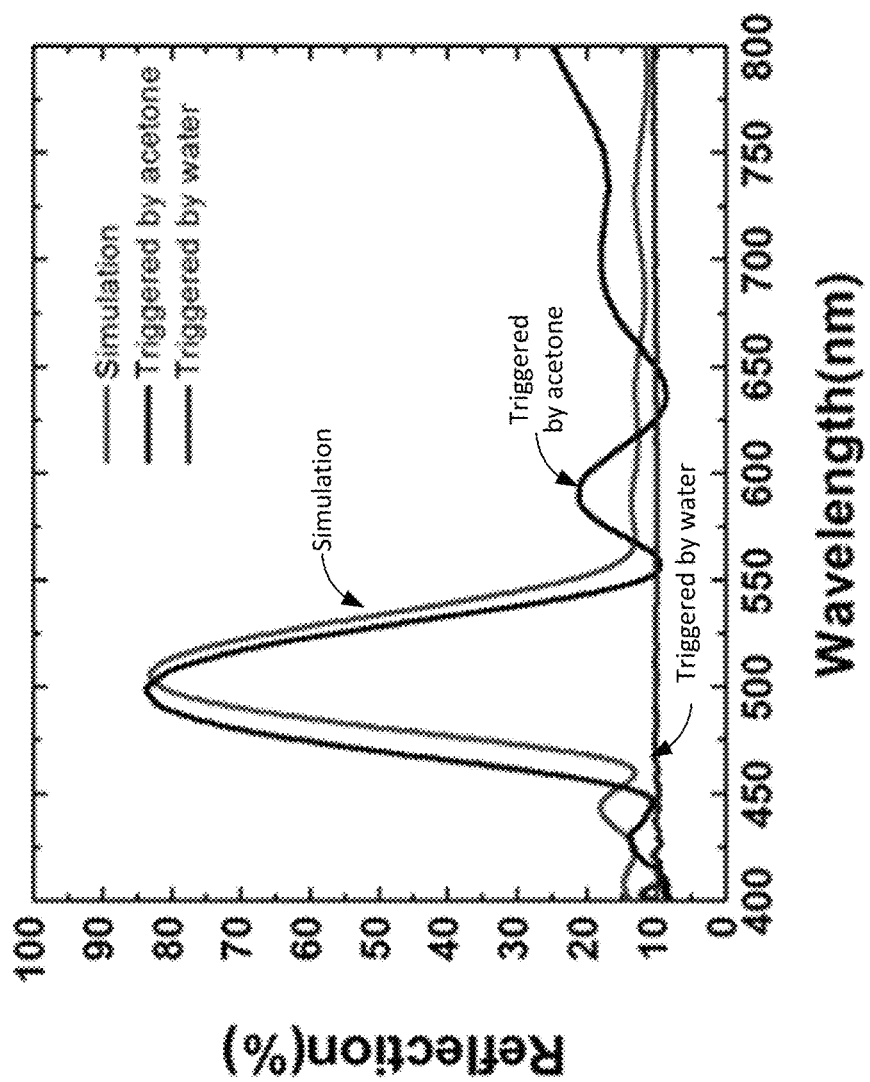
Fig. 1.2

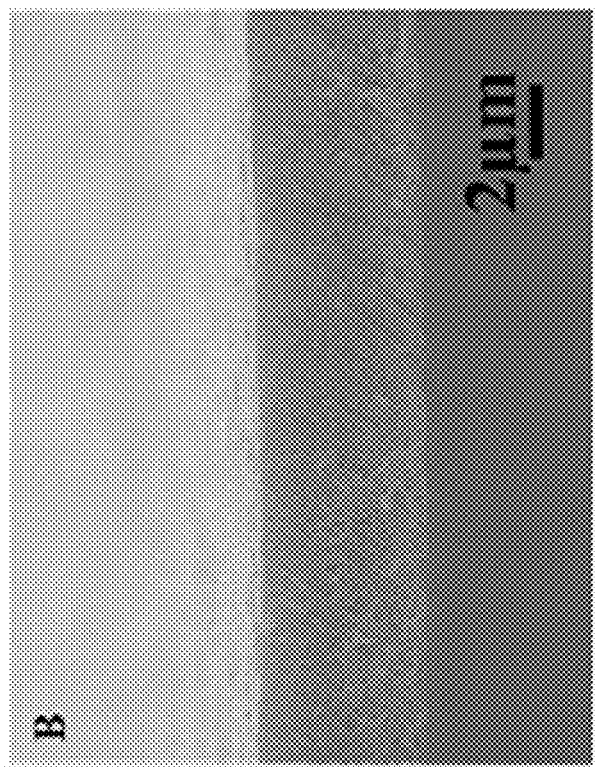
Fig. 1.3B
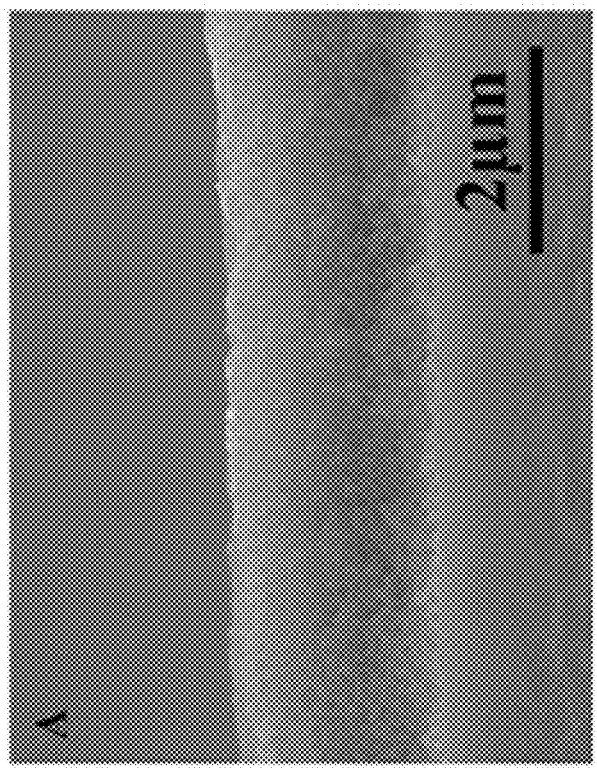
Fig. 1.3A

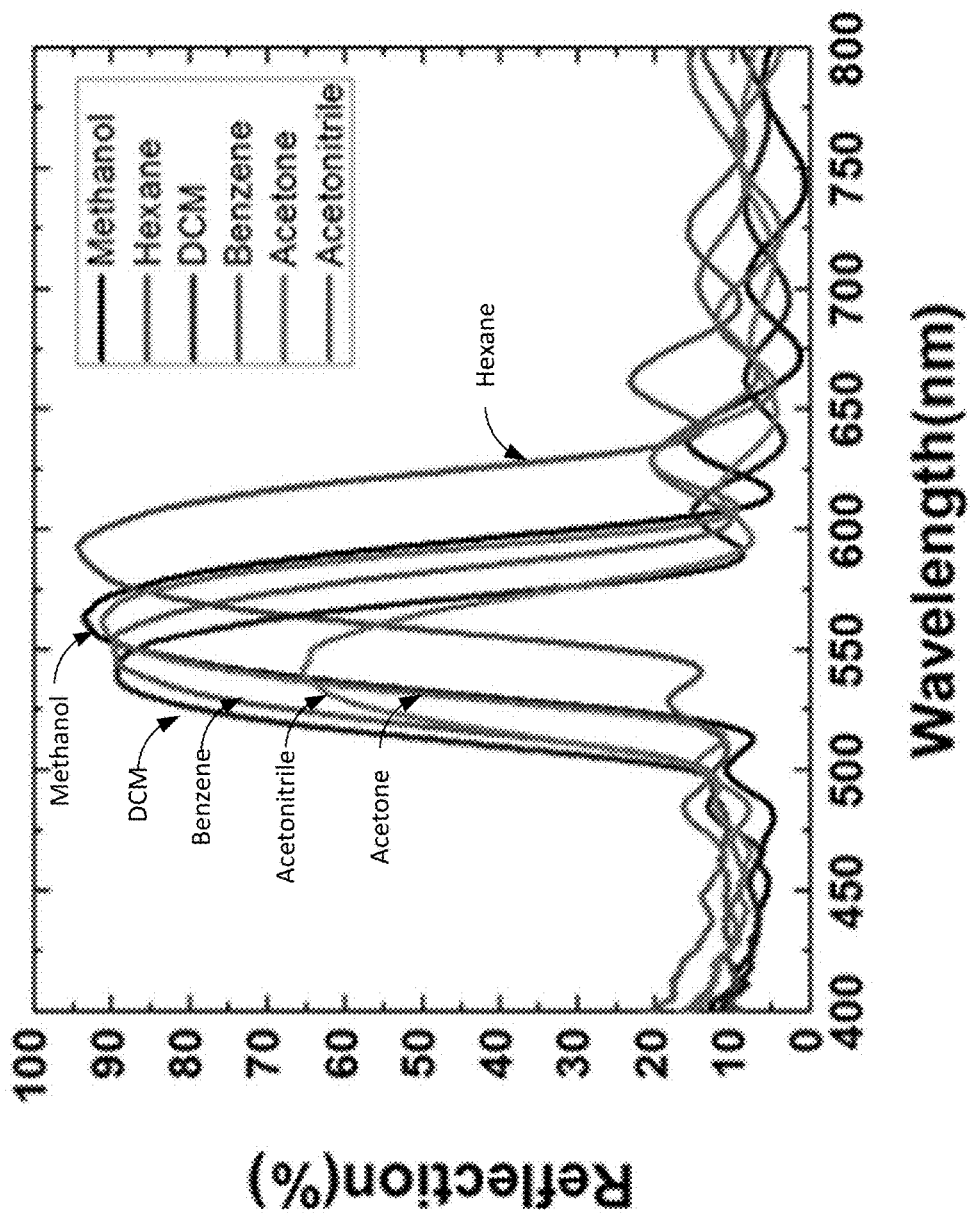
Fig. 1.4

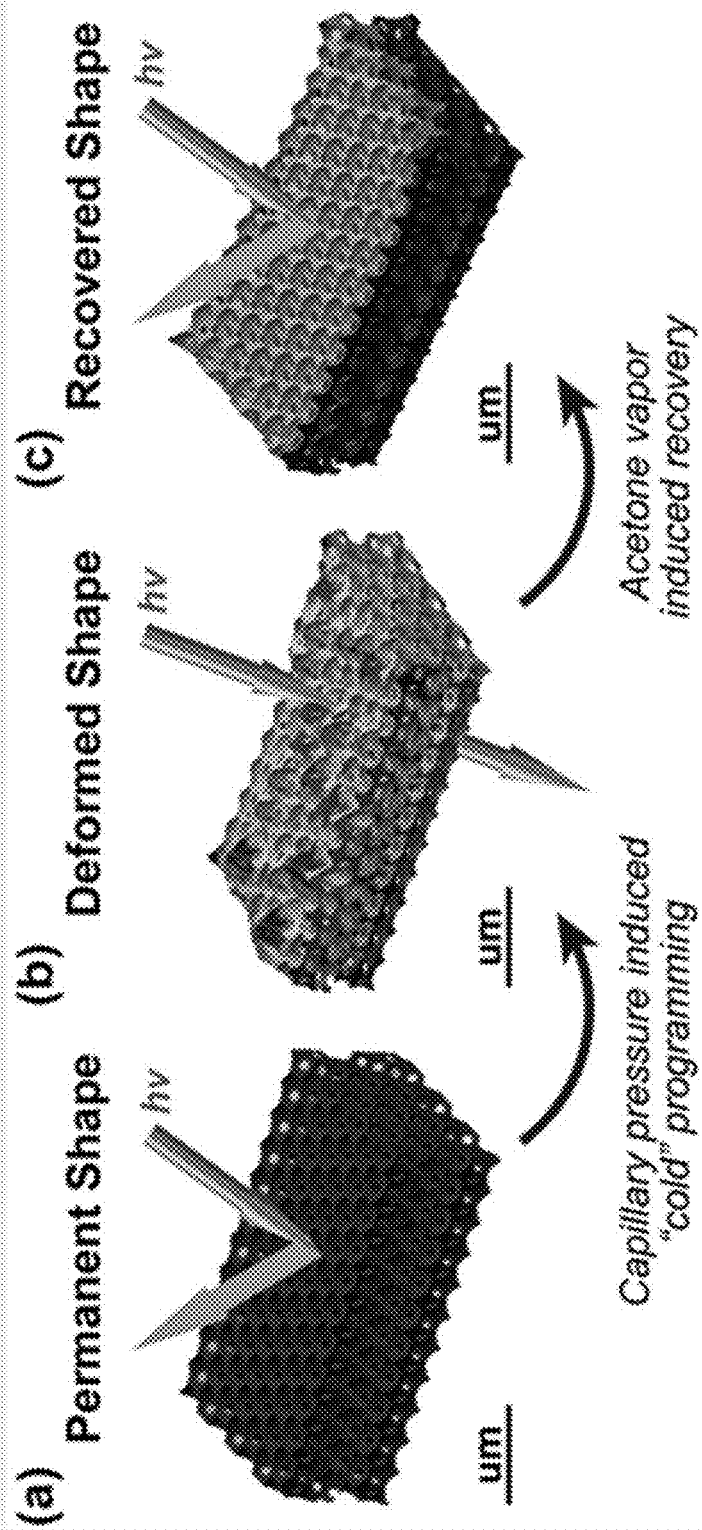
Fig. 2.1

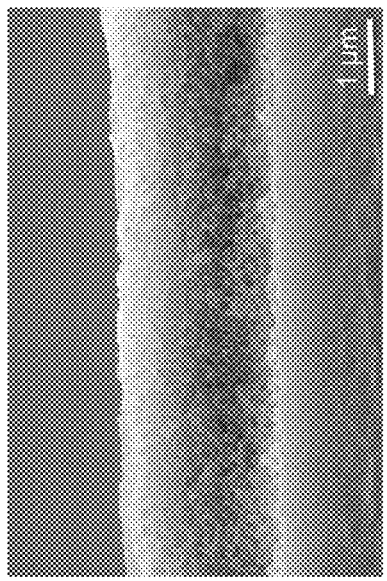
Fig. 2.2B
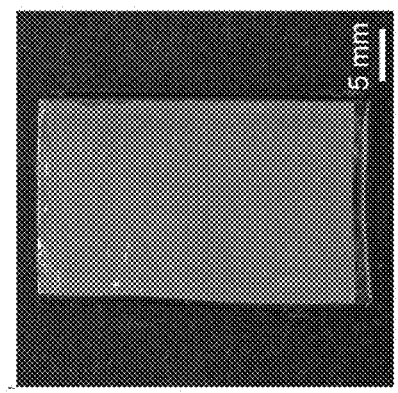
Fig. 2.2A
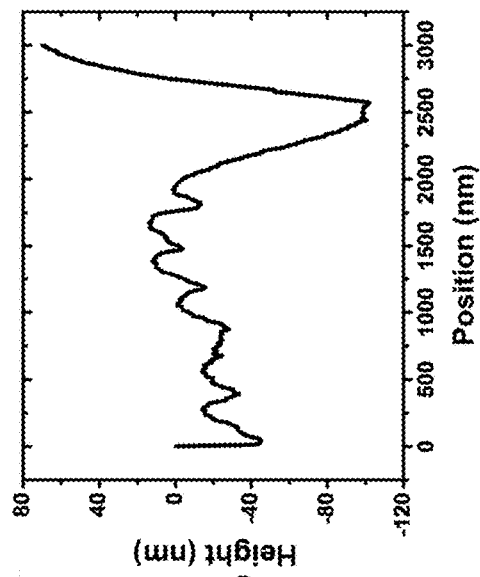
Fig. 2.2D
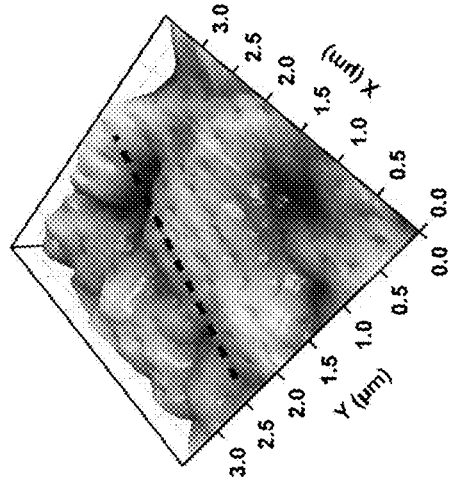
Fig. 2.2C

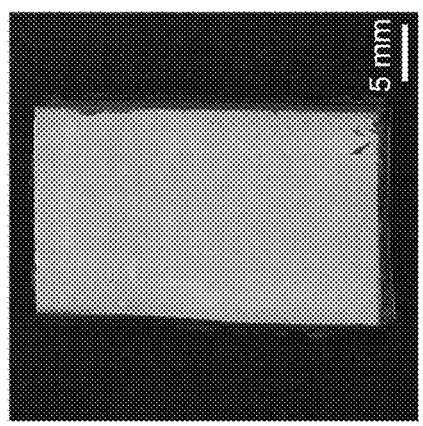
Fig. 2.3A
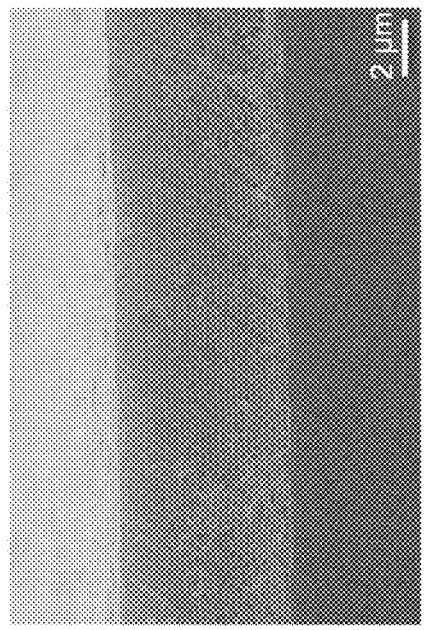
Fig. 2.3B
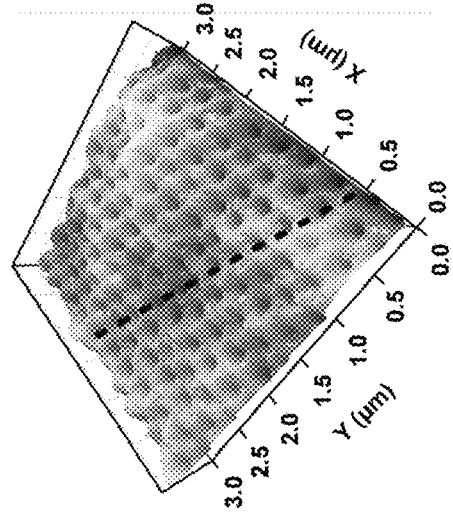
Fig. 2.3C
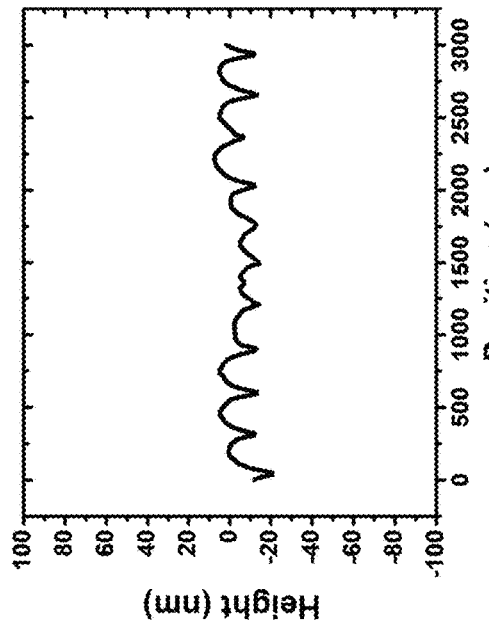
Fig. 2.3D

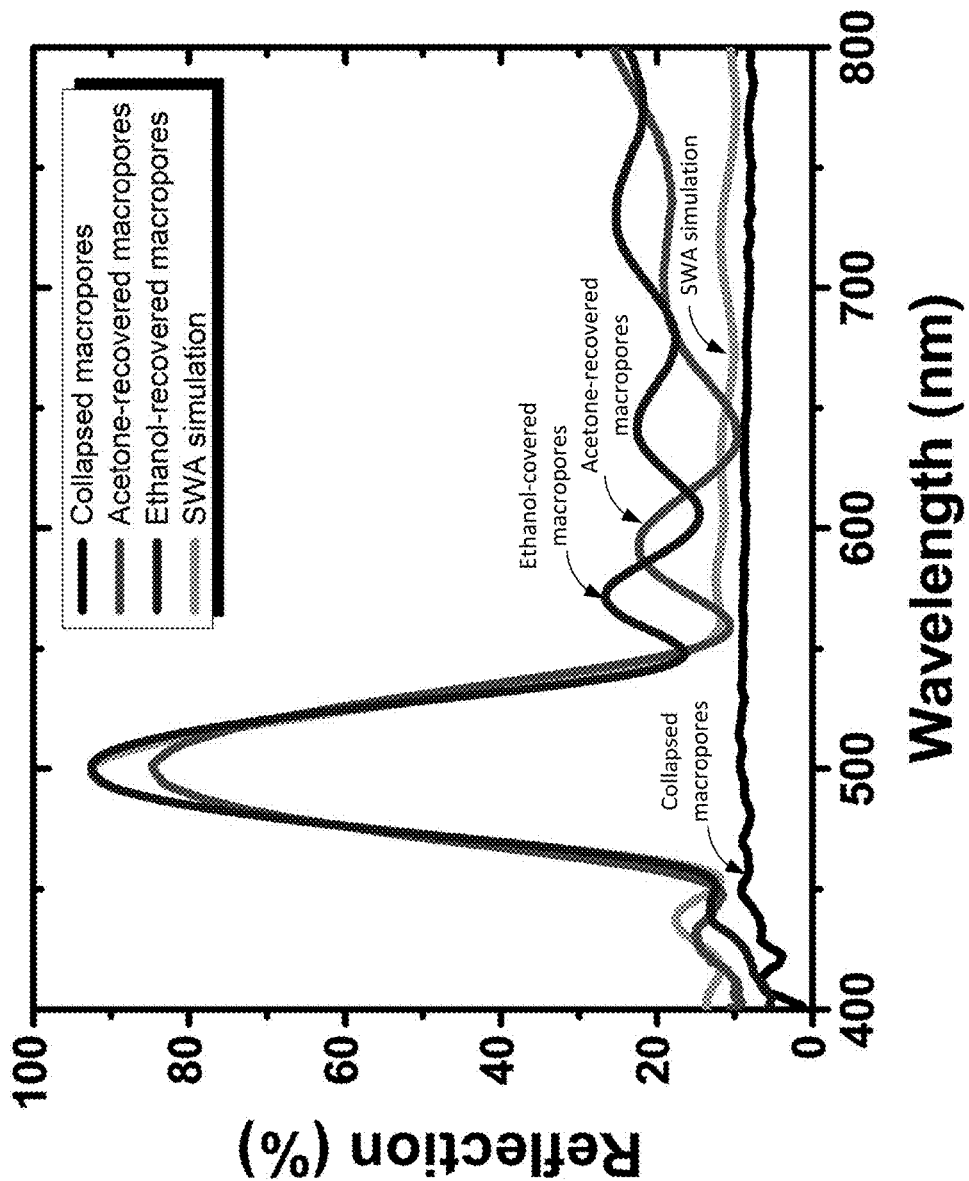
Fig. 2.4

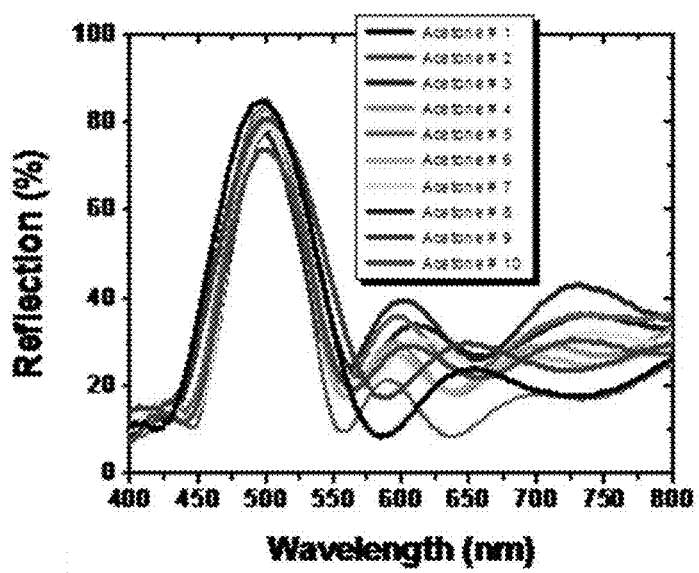
Fig. 2.5A
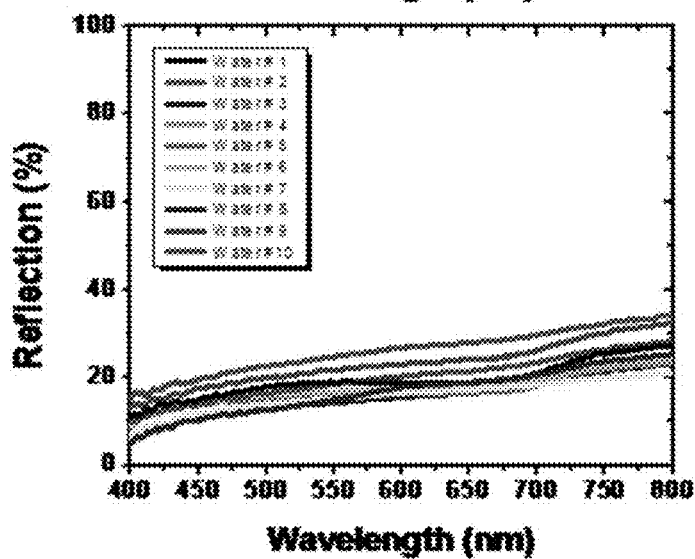
Fig. 2.5B
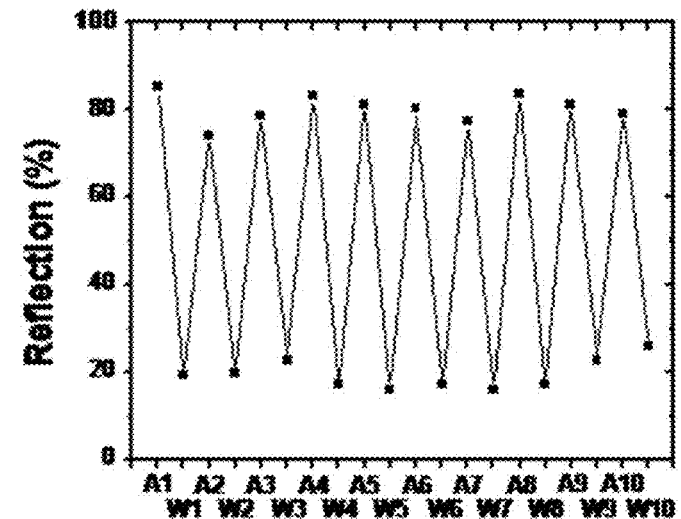
Fig. 2.5C

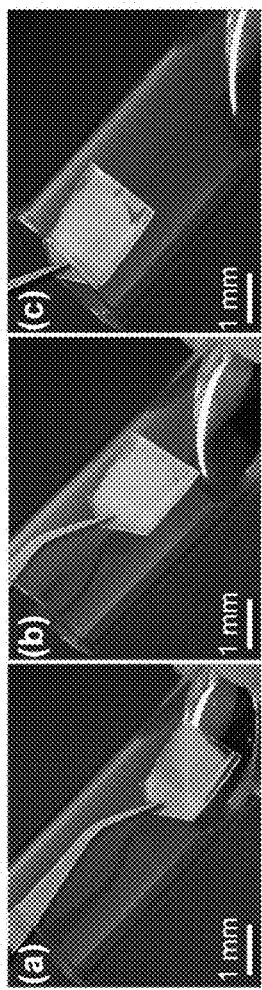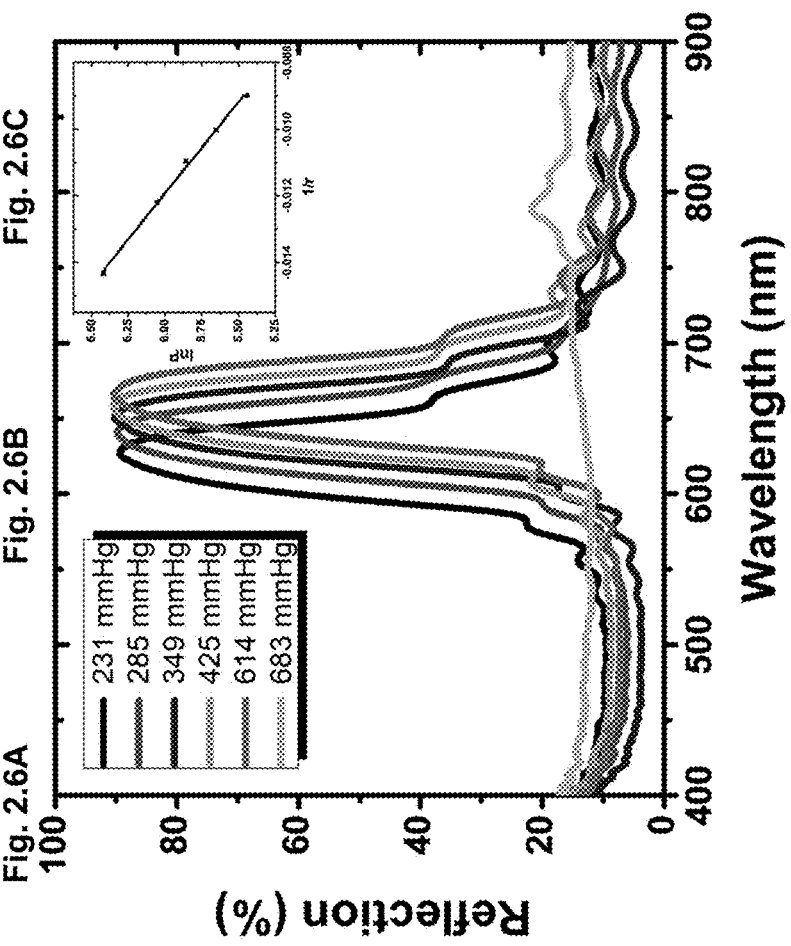
Fig. 2.6A  Fig. 2.6B  Fig. 2.6C
Fig. 2.6D

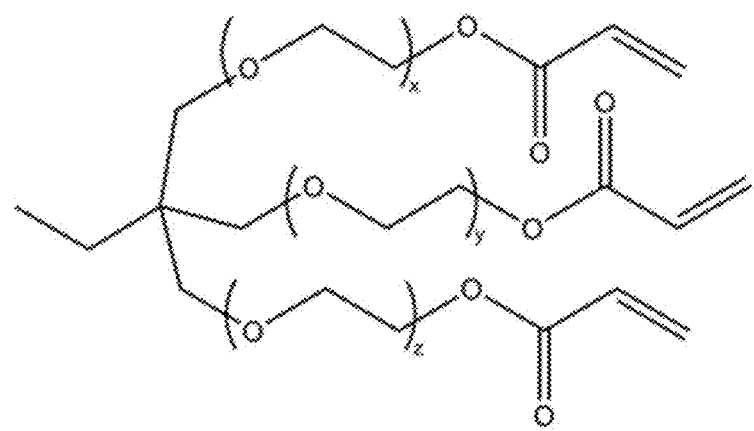
Fig. 2.7A
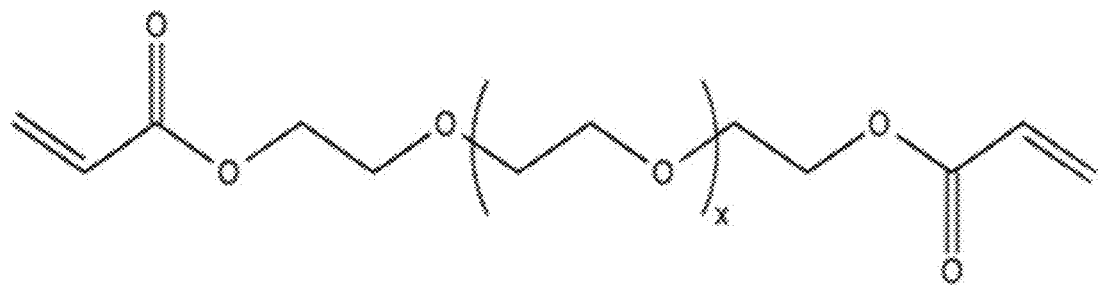
Fig. 2.7B

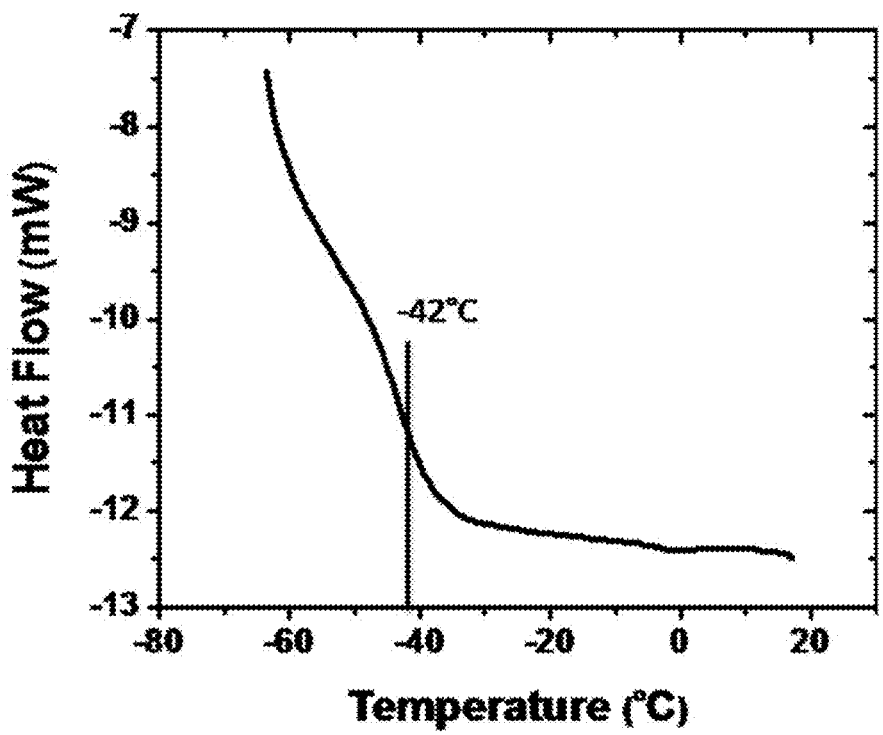
Fig. 2.8
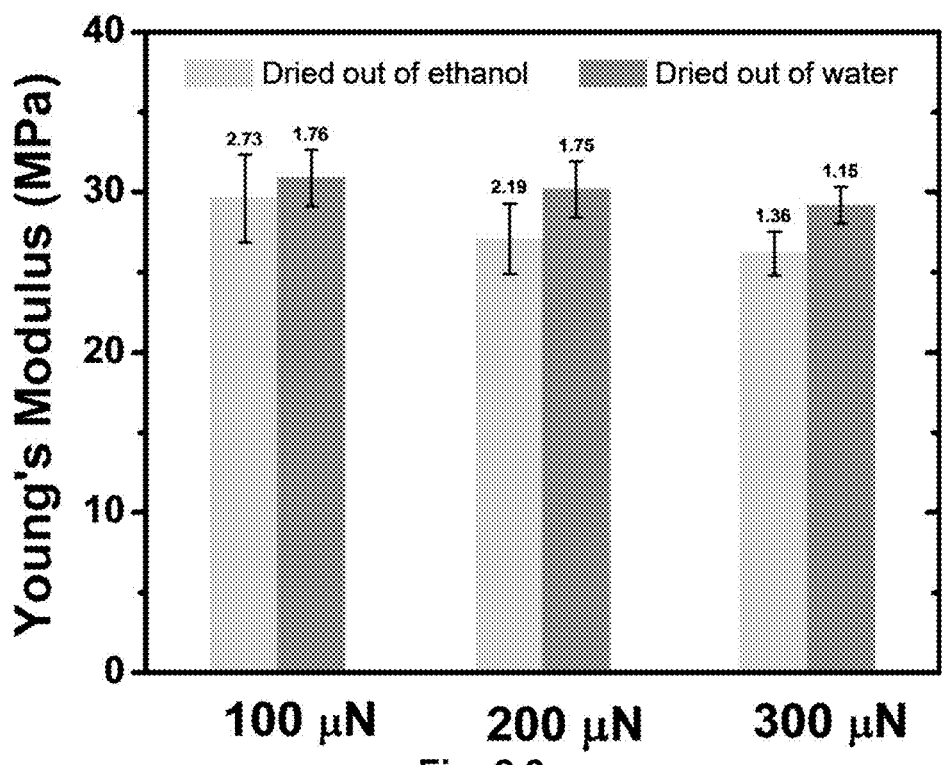
Fig. 2.9

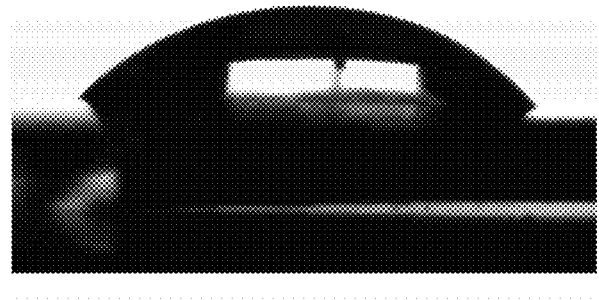
Fig. 2.10A
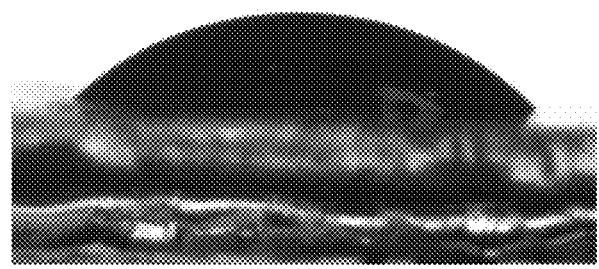
Fig. 2.10B
Fig. 2.10C

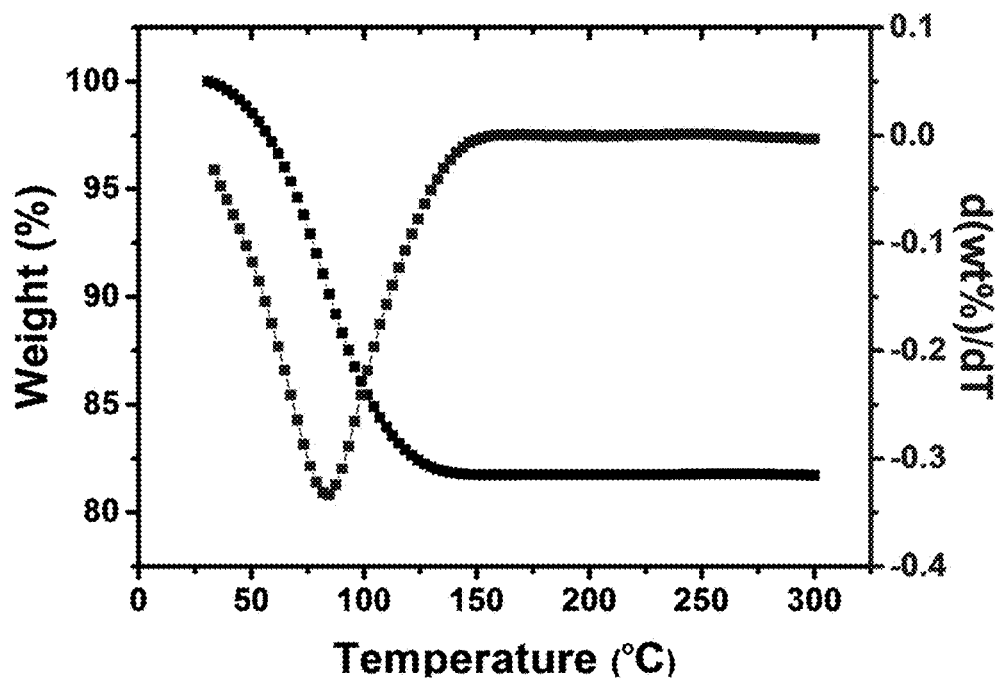
Fig. 2.11A
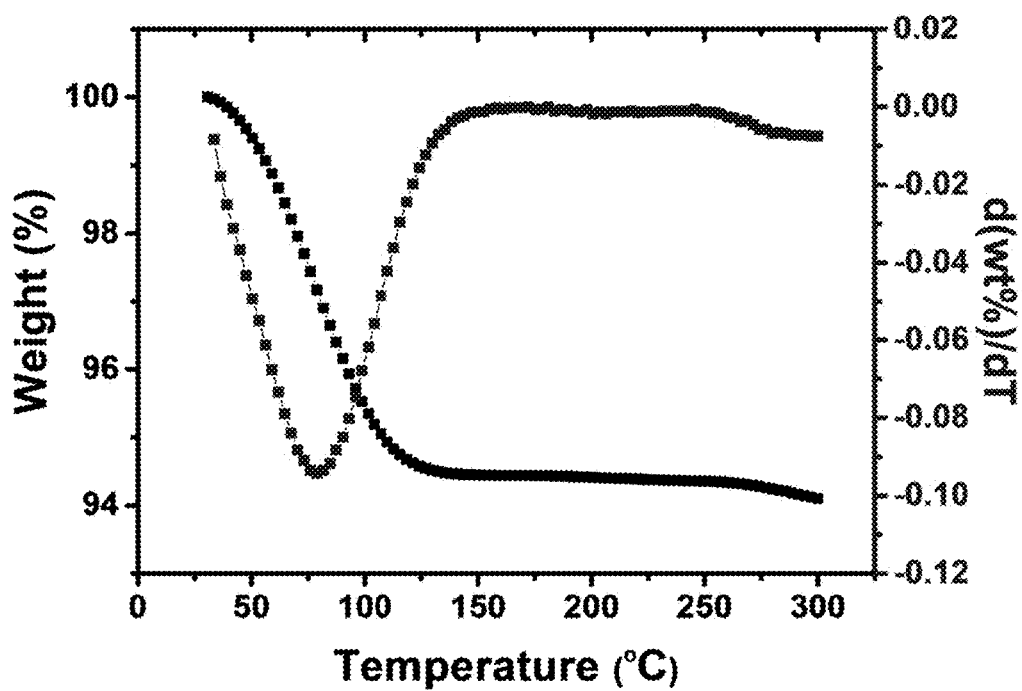
Fig. 2.11B

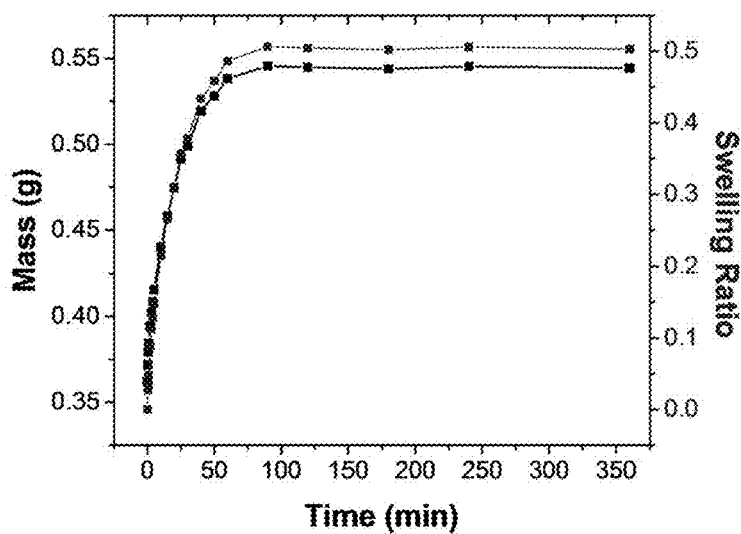
Fig. 2.12A
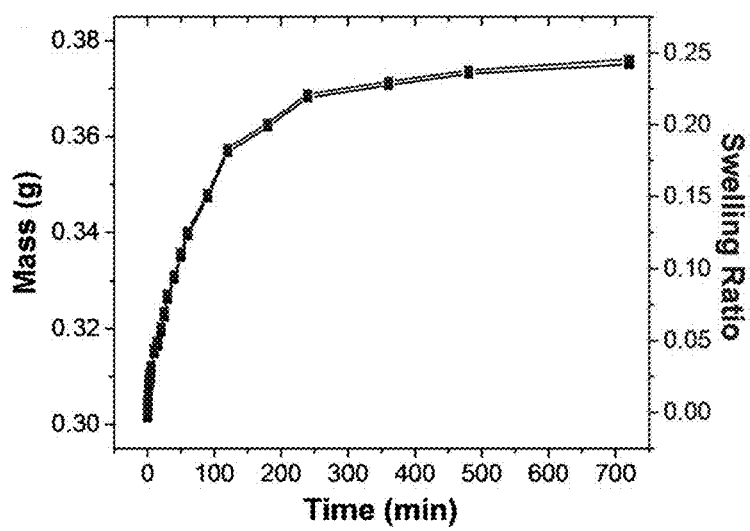
Fig. 2.12B
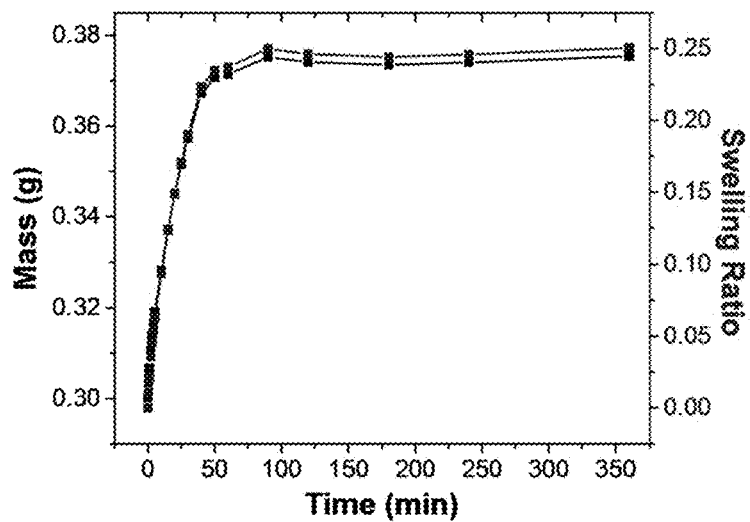
Fig. 2.12C

MACROPOROUS PHOTONIC CRYSTAL MEMBRANE, METHODS OF MAKING, AND METHODS OF USE

CROSS-REFERENCE TO RELATED APPLICATIONS

This application claims the benefit of and priority to U.S. Provisional Application Ser. No. 62/158,566, having the title "MACROPOROUS PHOTONIC CRYSTAL MEMBRANE, METHODS OF MAKING, AND METHODS OF USE," filed on May 8, 2015, the disclosure of which is incorporated herein in by reference in its entirety.

FEDERAL SPONSORSHIP

This invention was made with Government support under Contract/Grant No. 1300613, awarded by the National Science Foundation and under Contract/Grant No. NNX14AB07G, awarded by NASA. The Government has certain rights in this invention.

BACKGROUND

Shape memory polymers (SMPs) are a class of smart materials that can recover back to their "memorized" permanent shapes from temporary configurations in response to an external stimulus, such as heat, light, solvent, electric and magnetic fields. Traditional thermoresponsive shape memory (SM) effect is usually achieved in three steps including programming, storage, and recovery. The recovery time for bulk thermoresponsive SMPs is usually long, which impedes many applications that require fast response speed.

SUMMARY

In accordance with the purpose(s) of the present disclosure, as embodied and broadly described herein, embodiments of the present disclosure, in one aspect, relate to macroporous photonic crystal membranes, structures including macroporous photonic crystal membranes, devices including macroporous photonic crystal membranes, methods of using macroporous photonic crystal membranes, methods of making macroporous photonic crystal membranes, and the like.

Embodiments of the present disclosure provide for a structure, among others, that includes: a macroporous photonic crystal membrane including a three dimensional array of macropores, wherein a three dimensional polymer framework separates the macropores, wherein the polymer framework is made of a copolymer of two oligomers, wherein the two oligomers are ethoxylated (20) trimethylolpropane triacrylate (ETPTA 20) and polyethylene glycol (600) diacrylate (PEGDA 600), wherein when the macropores are in a collapsed state the macroporous photonic crystal membrane is substantially transparent, wherein when the macropores are in an uncollapsed state the macroporous photonic crystal membrane has an iridescent color. In an embodiment, the copolymer has a glass transition temperature of about −40° C. to −42° C. In an embodiment, the macroporous photonic crystal membrane has the characteristic of when exposed to a liquid, the uncollapsed macropores transform to their collapsed state. In an embodiment, the macroporous photonic crystal membrane has the characteristic of when the macropores are exposed to a vapor, the macropores transform into an uncollapsed state.

Embodiments of the present disclosure provide for a method of making a structure, among others, that includes: disposing nanoparticles onto a surface to form a three dimensional array of particles; introducing a prepolymer mixture to the array of particles; polymerizing the prepolymer mixture to form a polymer framework around the three dimensional array of particles; and removing the particles to form a three dimensional array of macropores in a macroporous photonic crystal membrane, wherein a three dimensional polymer framework separates the macropores, wherein the two oligomers are ethoxylated (20) trimethylolpropane triacrylate (ETPTA 20) and polyethylene glycol (600) diacrylate (PEGDA 600), wherein when the macropores are in a collapsed state the macroporous photonic crystal membrane is substantially transparent, wherein when the macropores are in an uncollapsed state the macroporous photonic crystal membrane has an iridescent color. In an embodiment, the copolymer has a glass transition temperature of about −40° C. to −42° C. In an embodiment, the macroporous photonic crystal membrane has the characteristic of when exposed to a liquid, the uncollapsed macropores transform to their collapsed state. In an embodiment, the macroporous photonic crystal membrane has the characteristic of when the macropores are exposed to a vapor, the macropores transform into an uncollapsed state.

Embodiments of the present disclosure provide for a method, among others, that includes: providing a macroporous photonic crystal membrane including a three dimensional array of macropores, wherein a three dimensional polymer framework separates the macropores, wherein the macropores are in a collapsed state, wherein when the macropores are in the collapsed state the macroporous photonic crystal membrane is substantially transparent, exposing the macropores to a vapor, and transforming the macropores transform from the collapsed state into an uncollapsed state, wherein the macroporous photonic crystal membrane has an iridescent color in the uncollapsed state. In an embodiment, the polymer framework is made of a copolymer of two oligomers, wherein the two oligomers are ethoxylated (20) trimethylolpropane triacrylate (ETPTA 20) and polyethylene glycol (600) diacrylate (PEGDA 600). In an embodiment, the copolymer has a glass transition temperature of about −40° C. to −42° C.

Other compositions, structures, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1.1A-B are photographs showing the basic principle of embodiments of the present disclosure. A colorless polymer film (1.1A) momentarily changed color to an iridescent green color (1.1B) when exposed to an acetone vapor.

FIG. 1.2 shows the experimental (black and blue (medium color)) and theoretical (red (light color)) optical reflection spectra obtained from a macroporous membrane dried out of water (blue), a recovered macroporous membrane triggered by acetone (red).

FIGS. 1.3A-B are scanning electron microscopy images of the samples with disordered macropores (1.3A) and acetone-triggered, 3-D ordered macropores (1.3B).

FIG. 1.4 shows the optical reflection spectra obtained from the same macroporous polymer membrane when exposed to different vapors.

FIG. 2.1 is a schematic illustration showing the SM effects of the new vapor-responsive SMP. Step a) Thin macroporous SMP photonic crystal with 3-D ordered structure can diffract light with specific wavelengths. Step b) The unusual "cold" programming process deforms the ordered macropores into disordered array with rough surface and no light diffraction. Step c) The recovery of the permanent photonic crystal structure can be triggered by exposing the deformed membrane to various organic vapors (e.g., acetone).

FIG. 2.2A is a photograph of a macroporous SMP membrane with 280 nm macropores after drying out of water. FIG. 2.2B is cross-sectional SEM image of the sample. FIG. 2.2C AFM scan of the sample surface. FIG. 2.2D is a height profile of the dashed line in 2.2C.

FIG. 2.3A is a photograph of a macroporous SMP membrane with 280 nm macropores after exposing to an acetone vapor. FIG. 2.3B is a cross-sectional SEM image of the sample. FIG. 2.3C is an AFM scan of the sample surface. FIG. 2.3D is a height profile of the dashed line in 2.3C.

FIG. 2.4 shows a normal-incidence optical reflection spectra comparing a macroporous SMP membrane with 280 nm macropores dried out of water, liquid ethanol, and acetone vapor. The calculated spectrum using a scalar-wave approximation (SWA) model is also shown to compare with the experimental results.

FIG. 2.5A is a normal-incidence optical reflection spectra obtained from a macroporous SMP membrane with 280 nm macropores exposed to acetone vapor for 10 times. FIG. 2.5B shows a normal-incidence reflection spectra of the same sample after drying out of water for 10 times. FIG. 2.5C shows reflection amplitudes of the spectra in 2.5A and 2.5B taken at 500 nm wavelength.

FIGS. 2.6A-C are photographs showing a macroporous SMP membrane exposed to acetone vapor above liquid acetone at different locations. FIG. 2.6D is a normal-incidence optical reflection spectra obtained from a macroporous SMP membrane exposed to acetone vapors with different vapor partial pressures. Inset showing dependence of InP vs the reciprocal of the radius of curvature of the condensed acetone films. The pressure is in unit of mmHg and the radius of curvature is in unit of nm.

FIG. 2.7A shows the molecular structure of ethoxylated (20) trimethylolpropane triacrylate (ETPTA 20, x+y+z=20). FIG. 2.7B molecular shows the structure of polyethylene glycol (600) diacrylate (PEGDA 600, x=12).

FIG. 2.8 demonstrates a typical differential scanning calorimetry (DSC) plot of a macroporous ETPTA 20-co-PEGDA 600 copolymer with 1:3 ratio.

FIG. 2.9 is a graphical comparison of the Young's modulus of the ethanol-dried (left columns) and water-dried (right columns) macroporous ETPTA 20-co-PEGDA 600 (1:3 ratio) membranes indented with different forces.

FIGS. 2.10A-C show water drop profiles on ETPTA 20-co-PEGDA 600 (1:3 ratio) SMP membranes. 2.10A is bulk membrane with flat surface. FIG. 2.10B is a macroporous membrane with collapsed 280 nm macropores (dried out water). FIG. 2.10C is macroporous membrane with open macropores recovered by acetone vapor exposure.

FIGS. 2.11A-B illustrate thermogravimetric analysis of ETPTA 20-co-PEGDA 600 (1:3 ratio) SMP membranes. FIG. 2.11A shows a fresh membrane dried out of water. FIG. 2.11B shows the same membrane after storage at ambient conditions for 2 days.

FIGS. 2.12A-C show mass and swelling ratio of macroporous ETPTA 20-co-PEGDA 600 (1:3 ratio) SMP membranes immersed in different solvents for various durations: FIG. 2.12A) water, FIG. 2.12B), ethanol, FIG. 2.12C), acetone.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of environmental engineering, biology, chemistry, materials science, mechanical engineering, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by volume, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequences where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DISCUSSION

In accordance with the purpose(s) of the present disclosure, as embodied and broadly described herein, embodiments of the present disclosure, in one aspect, relate to macroporous photonic crystal membranes, structures including macroporous photonic crystal membranes, devices including macroporous photonic crystal membranes, methods of using macroporous photonic crystal membranes, methods of making macroporous photonic crystal membranes, and the like.

In an embodiment, the macroporous photonic crystal membrane can be used as a vapor-responsive shape memory polymer, where the mechanical properties of the macroporous photonic crystal membrane can be tuned by controlling the ratio of the co-polymers used to form the macroporous photonic crystal membrane. In particular, the macroporous photonic crystal membrane includes an array of macropores that are in a collapsed state (e.g., the void volume of the macropores is reduced close to 0) or an uncollapsed state (e.g., the voids of the macropores are at full or near full three-dimension volume (e.g., the diameter (or longest dimension) of the spherical macropores of about 100 nm to 600 nm)). In an embodiment, the macroporous photonic crystal membrane can have about 2,000 to 20,000 voids/mm or about 2,000 to 10,000 voids/mm. In the collapsed state the macroporous photonic crystal membrane is substantially transparent or translucent (e.g., a pale white color) or transparent or translucent, while when the membranes have transformed from the collapsed state to the uncollapsed state, the macroporous photonic crystal membrane has an iridescent color that is visible with the naked eye (e.g., a detector is not needed to perceive the change in state, which is advantageous for inexpensive and chromogenic detectors/sensors).

When a liquid such as water is applied to an area of the macroporous photonic crystal membrane and then dried, the uncollapsed macropores or fully formed state (e.g., having maximum void volume) transform to their collapsed state (e.g., having minimum or zero void volume).

When the macroporous photonic crystal membrane is exposed to a vapor of a solvent (e.g., acetone, methanol, dichloromethane, toluene, benzene, and ethanol) and the macropores are in the collapsed state, the macropores are transformed into their uncollapsed state or fully open state. And during the transformation the macroporous photonic crystal membrane (the macropores in the collapsed state) changes from a transparent color or substantially clear appearance to an iridescent color. In particular, the iridescent color is caused by Bragg diffraction of visible light. In an embodiment, each gas vapor can result in a different Bragg diffraction of visible light, which allows for the determination of the presence of different vapors. In other words, embodiments of the present disclosure can distinguish between or among different gas vapors.

An advantage of an embodiment of the present disclosure is that the process for making the macroporous photonic crystal membrane is simple, scalable, and inexpensive. In addition, embodiments of the present disclosure can be used in applications such as portable and reusable vapor sensors that show a striking and easily identifiable color change that is clearly perceivable to the naked eye so that additional instrumentation to measure a color change is not needed. Sensors including macroporous photonic crystal membrane can be placed where one wants to be alerted to the presence of one or more types of vapors. For example, a sensor can be used to measure acetone in a person's breath for simple diabetes testing.

In another embodiment, a sensor can be used by first responders to quickly screen for one or more types of vapors (e.g., acetone, methanol, dichloromethane, toluene, benzene, and ethanol). In an additional embodiment, a sensor can be used in new construction to test for the presence of vapors (e.g., acetone, methanol, dichloromethane, toluene, benzene, and ethanol).

Embodiments of the present disclosure do not require extensive training to read the sensor and understand that one or more vapors may be present or that the sensor was exposed to one or more vapors in the area of the sensor. Once the sensor has detected the presence of a vapor, the macroporous photonic crystal membrane can be reset and the sensor reused by rinsing the macroporous photonic crystal membrane with a liquid such as water and dried.

In an embodiment, the thickness of the macroporous photonic crystal membrane can vary depending on the state of the macropores and the number of maropores along a plane perpendicular to the length of the macroporous photonic crystal membrane. In an embodiment the macroporous photonic crystal membrane can have a thickness of about 1 micrometer to 300 micrometers. In an embodiment, the dimensions of the macroporous photonic crystal membrane can be selected based on a particular application.

In an embodiment, the macroporous photonic crystal membrane can include a co-polymer of a pair of ethoxylated (20) trimethylolpropane triacrylate (ETPTA 20) and polyethylene glycol (600) diacrylate (PEGDA 600) monomers that have low glass transition temperatures (e.g., $T_g$<room temperature). In an embodiment, the ratio of ETPTA 20 and PEGDA 600 can be about 1:1 to 1:10. In an embodiment, the polymer framework is a co-polymer of ETPTA 20 and PEGDA 600 with 1:3 volumetric ratio. The mechanical properties (e.g., rigidity and strength) of the resulting co-polymers can be tuned by controlling the ratio of these two monomers. A higher ratio of PEGDA 600 leads to a softer polymer. For instance, a co-polymer membrane of ETPTA 20-co-PEGDA 600 with a ratio of about 1:6 is significantly softer than a film with about 1:3 ratio. In an embodiment, the ratio of ETPTA 20 and PEGDA600 can be about 1:1 to 1:6.

In an embodiment, the macroporous photonic crystal membrane can include an ordered three dimensional array of macropolymers. In an embodiment, the macropores are arranged in a face-centered cubic (F.C.C.) geometry. In an embodiment, the macropolymers can be stacked directly on top of one another or the stacking can be offset. In an embodiment, the array can be randomly ordered. In an embodiment, the thickness of the macroporous photonic crystal membrane can include about 2 to 1000 monolayers of macropores.

In an embodiment, the distance at least two pairs of adjacent macropores can be substantially the same (e.g., about 100 nm to 600 nm). In an embodiment, the number of unique pairs can be about 10, 100, 1000, 10,000, 100,000, 1,000,000, 100,000,000, 100,000,000, to about 10, 100, 1000, 10,000, 100,000, 1,000,000, 100,000,000, 100,000, 000, $1\times10^{10}$, $1\times10^{12}$, $1\times10^{15}$, $1\times10^{17}$, or $1\times10^{20}$ and any set of ranges (e.g., about 10,000 to 100,000, about 100 to $1\times10^{10}$, etc.) within these numbers or subranges (e.g., about 15 to 200,000, 2,500,000 to $3\times10^{12}$, etc.) within these numbers.

In an embodiment, the distance between each pair of adjacent macropores can be substantially the same. In an embodiment, the distance between a portion of the pairs of adjacent macropores is substantially the same. In an embodiment, the "portion" can be about 50% or more, about 60% or more, about 70% or more, about 80% or more, about 90% or more, about 99% or more, or about 100%, over a defined area of the macroporous photonic crystal membrane. In an embodiment, the defined area can include about 50% or more, about 60% or more, about 70% or more, about 80% or more, about 90% or more, about 95% or more, about 99% or more, or about 100%, of the area of the macroporous photonic crystal membrane. The term "substantially" in these contexts can mean about 50% or more, about 60% or more, about 70% or more, about 80% or more, about 90% or more, about 99% or more, or about 100%. The term "adjacent" refers to two macropores next to one another without a macropore separating them in the same macroporous photonic crystal membrane.

In an embodiment, the three dimensional polymer framework separates the macropores. In an embodiment, the diameter of substantially all of the macropores can be substantially equivalent. In an embodiment, the diameter can be about 100 nm to 600 nm when fully uncollapsed. The term "substantially" in this context can mean about 50% or more, about 60% or more, about 70% or more, about 80% or more, about 90% or more, about 99% or more, or about 100%.

In an embodiment, two sets of macropores of different diameters can be present that form an array of macropores. In an embodiment, a first pair of macropores has a first diameter and a second pair of macropores has a second diameter, where the first diameter and the second diameter are not the same. The array of macropores can have a plurality of first sets and second sets. In another embodiment, the macroporous photonic crystal membrane can include three or more sets of such macropores each having different diameters.

In an embodiment, the macroporous photonic crystal membrane can be formed by disposing particles onto a surface to form an array of particles. In an embodiment, a monomer mixture can be disposed on a surface using capillary forces or using a process such as a doctor blade coating process, tape casting, or applying a simple shear force by two plates with a controlled gap in between. The particles can be aligned in a three dimensional ordered colloidal crystal array, e.g., the particles can be located in crystalline lattices of, for example, a face-centered cubic (f.c.c.), hexagonal-centered cubic (h.c.p.) crystals, or the like. After the monomer mixture is disposed on the particle array, the monomer mixture can be polymerized to form a photonic crystal membrane having particles disposed in the polymer membrane. In an embodiment, the polymerization can be photopolymerization, thermopolymerization, or a combination thereof.

Subsequently, a portion (e.g., about 50%, 60%, 60%, 80%, 90%, 95%, 99% or more, or about 100%) or all of the particles can be removed to form the photonic crystal membrane. In an embodiment, the particles can be removed by a process that does not alter the polymer. The type of process used to remove the particles depends, at least in part, upon the type of particle and the polymer. In an embodiment, the macroporous photonic crystal membrane is formed by dissolving the particles using an acid solution such as, but not limited to, hydrofluoric acid (e.g., for silica nanoparticles). The macroporous photonic crystal membrane including an array of macropores is formed once the particles are removed.

As mentioned above, the macropores are made from the removal of one or more particles. In an embodiment, the particles are disposed on top of one another in the polymer membrane, and when the particles are removed, a macropore is formed in the place of each particle. In an embodiment, the macropores are distinct from one another and in another embodiment the macropores are interconnected to form interconnected volumes that can form channels within and/or through the macroporous photonic crystal membrane.

In an embodiment the monomer mixture can include two or more monomers such as those described herein, wherein each monomer can be about 5 to 95 weight percent of the monomer mixture. In an embodiment the prepolymer mixture can include ETPTA 20 and PEGDA 600. In an embodiment, the volumetric ratio of ETPTA 20 to PEGDA 600 can be about 1:1 to 1:10 or about 1:2 to 1:6. In addition, the monomer mixture can include a polymer initiating agent such as a photoinitiator (e.g., 2-hydroxy-2-methyl-1-phenyl-1-propanone, azobisisobutyronitrile, or and 2,2-dimethoxy-2-phenylacetophenone). The amount of initiator used depends upon the polymerization process, the monomers, and the like.

Once the monomer is polymerized, a three dimensional polymer framework is formed around the particles. After the particles are removed, the three dimensional polymer framework (e.g., based on crystalline lattices of the particles, for the polymer framework is based on a face-centered cubic (f.c.c.), hexagonal-centered cubic (h.c.p.) crystals, or the like where the voids are at the positions where the particles were previously located) supports the macroporous photonic crystal membrane. The mechanical characteristics of the three dimensional polymer framework can be controlled by selection of the monomers, the ratio of the monomer, and the like. The dimensions of the three dimensional polymer framework can be controlled by the process of disposing the monomer/particle mixture on the substrate. In an embodiment, the thickness of the three dimensional polymer framework between adjacent nanoparticles can be about 100 nm to 600 nm.

In an embodiment, the particles can be of the same or different type and/or same or different size, depending on the use or purpose of the macroporous photonic crystal membrane. The selection of the type particle can depend upon the process for removing the particle, the type of polymer, and/or three dimensional polymer framework. The selection of the size can depend upon the process for removing the particles, the type of polymer, the polymer framework, the diameter of the desired macropores and channel, and the like. In an embodiment, two or more different types and/or sizes of particles can be selected. In an embodiment, two or more processes can be used to remove the particles (e.g., when two or more types of particles are used in the monomer/nanoparticle mixture). The type of particle can include silica nanoparticles, polymer latex nanoparticles, titania nanoparticles, CdSe nanoparticles, and other nanoparticles where the type selected has a uniform diameter. In an embodiment, the nanoparticles can have a diameter (or longest dimension) of about 10 nm to 1000 nm or about 100 nm to 600 nm.

Once the particles have been removed, the macropores can be collapsed by exposing the macroporous photonic crystal membrane to a liquid such as water and then evaporating the water. The macroporous photonic crystal membrane can be renewed and reused many times (e.g., 100 or 1000 times).

EXAMPLES

Now having described the embodiments of the present disclosure, in general, example 1 describes some additional embodiments of the present disclosure. While embodiments of the present disclosure are described in connection with example 1 and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

FIGS. 1.1A-B show the basic principle of the current invention. A colorless macroporous polymer membrane (FIG. 1.1A) with disordered macropores immediately changed color to a greenish film when exposed to an acetone vapor. When the colorful film is immersed in water and then dried out of it, the membrane changed back to the colorless state. This striking colorless to iridescent transition can be repeated many times (>100) with no apparent degradation in the quality of the membrane.

We characterized the optical properties of the samples in FIGS. 1.1A-B using optical reflection measurements and numerical simulations. FIG. 1.2 shows the experimental (black and blue curves) and theoretical (red curve) optical reflection spectra obtained from the samples in FIGS. 1.1A-B. The colorless sample in FIG. 1.1A (dried out of water with disordered macropores) does not show Bragg diffraction peak in the corresponding reflection spectrum (blue curve). By contrast, the iridescent sample in FIG. 1.1B which was exposed to acetone vapor exhibits a distinct Bragg diffraction peak around 500 nm wavelength. The experimental spectrum matches well with the simulated spectrum (red curve) using a scalar-wave approximation model. This model assumes perfect 3-D ordered macropores arranged in the macroporous membrane.

We conducted scanning electron microscope (SEM) analysis of the colorless and iridescent membranes shown in FIGS. 1.1A-B. FIG. 1.3A shows a typical cross-sectional SEM image of the colorless sample. It is apparent that the macropores are disordered. By contrast, the SEM image in FIG. 1.3B confirms that the acetone-triggered sample has 3-D highly ordered macropores that lead to the iridescent color of the sample in FIG. 1.1B.

To show the multiplexing capability of our new sensors, we conducted optical reflection measurements by exposing the same macroporous polymer membrane to various vapors. FIG. 1.4 shows the optical reflection spectra. It is clear that different vapors result in different optical response.

Example 2

Shape memory polymers (SMPs) are a class of smart materials that can recover back to their "memorized" permanent shapes from temporary configurations in response to an external stimulus, such as heat, light, solvent, electric and magnetic fields.[1-12] Compared with their alloy counterparts (e.g., nitinol alloy), SMPs have gained increased attention due to their dramatically larger strain storage and recovery (up to 800% vs. less than 8%), light weight, low cost, ease of synthesis, and biocompatibility.[1, 2, 4-6, 13] They have been extensively explored for a wide spectrum of technological applications, such as reconfigurable morphing structures,[14,15] smart textiles,[16,17] sensors and actuators,[18,19] self-healing materials,[20] surgical stents and sutures,[21,22] and implants for minimally invasive surgery.[23] Traditional thermoresponsive shape memory (SM) effect is usually achieved in three steps including programming, storage, and recovery.[6] Programming involves deforming a bulk SMP sample from its permanent shape to a temporary shape at a temperature higher than some specific transition temperatures ($T_{trans}$) of the polymer, such as melting temperature ($T_m$) or glass transition temperature ($T_g$). The deformed sample is then cooled below $T_{trans}$ to fix the temporary shape which can be stored at ambient conditions for a long period of time. Recovery to the permanent shape, which is caused by entropy elasticity, occurs when the sample is reheated to above $T_{trans}$.[5,6]

The recovery time for bulk thermoresponsive SMPs, which are mostly studied and employed in practical devices, is usually long.[5, 6, 13] This significantly impedes many applications that require fast response speed. Similar slow SM response is also suffered by many other types of SMPs activated through laser, solvent, electric field, infrared absorption and alternating magnetic field.[24-27] Indeed, most of these different SM activation mechanisms are still thermoresponsive as they depend on the generation of heat by various means to trigger the final shape recovery. Additionally, "hot" programming is generally utilized by almost every class of existing SMPs.[1-11, 13, 28, 29] By contrast, SMPs that can be "cold" programmed (i.e., deformed to a temporary shape at or below room temperature), which could greatly enhance the processability to accommodate broader application requirements (e.g., room temperature operations for the entire SM cycle), are rare.[30,31] Moreover, most of the current SMP applications leverage the macroscopic SM effects and the deformation length scale is usually large (on the order of centimeter or larger). However, an intriguing potential for many new applications, largely unexplored, is the ability of SMPs to memorize and change shape at nanoscale.[32,33] Furthermore, although a variety of solvents (e.g., water) can trigger SM recovery by effectively reducing $T_g$ of the polymer through the plasticizing effect,[34-39] vapor-responsive SMPs are uncommon.[40]

This Example discusses a new type of vapor-responsive SMP that enables unusual "cold" programming and instantaneous shape recovery at the nanoscale. These novel SMPs were discovered in the fabrication of macroporous polymer photonic crystals. Photonic crystals are periodic dielectric structures with a forbidden gap (or photonic band gap) for electromagnetic waves, analogous to the electronic band gap in semiconductors which lies at the heart of microelectronics.[41-43] Photons with energies lying in the photonic band gap (PBG) cannot propagate through the medium, providing unprecedented opportunities to control the flow of light in miniature volumes for a large variety of applications ranging from all-optical integrated circuits to diffractive optical devices (e.g., optical filters).[44,45] Tunable photonic crystals, whose lattice structures and PBGs can be adjusted by various stimuli, such as external pressure, electric and magnetic fields, solvents, vapors and metal ions, have been extensively investigated by using elastic materials (e.g., elastomers and gels).[46-64] However, the deformed photonic crystal structures cannot be memorized and they rapidly return to the original crystalline lattices once the external stimuli are released. Although smart SMPs could provide an unique opportunity to realize reconfigurable photonic crystals with bistable states (corresponding to the permanent and the temporary shapes of a SMP), these stimuli-responsive materials have rarely been used in previous photonic crystal studies.[65,66]

By integrating scientific principles drawn from two disparate fields that do not typically intersect—the fast-growing photonic crystal and SMP technologies, here we demonstrate that reconfigurable photonic crystals exhibiting striking chromogenic effects can be achieved by using a new type of vapor-responsive SMP. Interestingly, our recent work has shown that the SM recovery of the same type of SMP can also be rapidly triggered by applying an external contact pressure.[67] As illustrated by the scheme in FIG. 2.1, the permanent photonic crystal configuration used in the current work is a three-dimensional (3-D) periodic array of macropores. These macroporous SMP photonic crystals were farbricated by using 3-D highly ordered silica colloidal crystals as structural templates.[68,69] The templating colloidal crystals were assembled by the convective self-assembly technology using silica microspheres with diameter ranging from 200 to 600 nm.[70] The thickness of the resulting colloidal crystal was controlled to ~3-5 μM (or ~10-20 colloidal monolayers) by adjusting the concentration of the colloidal suspensions in the convective self-assembly process. The interstitial air in-between the silica microspheres was replaced by viscous oligomer mixtures of ETPTA 20 (MW 1176, viscosity 225 cps at 25° C., $T_g$~−40° C., refractive index ~1.470) and PEGDA 600 (MW 742, viscosity 90 cps at 25° C., $T_g$~−42° C., refractive index ~1.468) with varying volumetric ratios from 1:1 to 1:6. The molecular structures of these oligomers are shown in FIGS. 2.7A-B. The oligomer mixture was then photocured at ambient conditions and the templating silica microspheres were selectively dissolved in a hydrofluoric acid aqueous solution, leaving behind a free-standing macroporous ETPTA 20-co-PEGDA 600 copolymer membrane with crystalline arrays of macropores. The size of the templated macropores, which determines the color of the final macroporous photonic crystal, is defined by the diameter of the templating silica microspheres. Differential scanning calorimetric (DSC) measurements (see typical DSC plots of macroporous ETPTA 20-co-PEGDA 600 copolymer film with 1:3 ratio in FIG. 2.8) show the copolymers have $T_g$ close to those of the two oligomer components, indicating the crosslinked copolymers are rubbery at room temperature. When immersed in water, the templated macroporous SMP membrane shows pale iridescent colors at large viewing angles (>45°) caused by Bragg diffraction of visible light from the periodic arrays of polymer macropores filled with water (refractive index 1.333). This confirms the maintenance of the 3-D ordered structure of the original silica colloidal crystal throughout the templating process.

The unusual "cold" programming process occurred when the macroporous SMP membrane dried out of water. Surprisingly, the iridescent color of the macroporous photonic crystal disappeared, and the film became translucent with a pale white appearance (FIG. 2.2A). The typical cross-sectional scanning electron microscope (SEM) image of the water-dried sample in FIG. 2.2B shows no apparent ordering of the templated macropores, indicating an order-disorder transition during water evaporation. The atomic force microscopy (AFM) image (FIG. 2.2C) and the depth profile scanned across the line (FIG. 2.2D) illustrate that the surface of the dried membrane is rough. The root-mean-square (RMS) linear profile roughness ($R_q$) of the sample was determined to be 41.7±7.8 nm (Table 2.1). We attributed this order-disorder transition during water evaporation to the large capillary pressure induced by the high surface tension of water (72.75 mN/m at 20° C.), which is sufficient to compress the ordered elastic macropores into disordered arrays. According to the Young-Laplace equation, $P_c$=2γ cos θ/r, the capillary pressure ($P_c$) is proportional to the liquid/vapor surface tension (γ) and cos θ (θ is the contact angle of the liquid on the pore surface); while inversely proportional to the radius of the pores (r).[71] Therefore, $P_c$ can be reduced by using a solvent with a low surface tension (e.g., ethanol with γ~22.39 mN/m at 20° C.), or by increasing the size of the pores. When $P_c$ is small compared with the elastic modulus (or Young's modulus, E) of the copolymer membrane, we expect the templated SMP macropores will remain in the original 3-D highly ordered structure, instead of being squeezed into disordered arrays. This speculation was supported by two experimental evidences. First, iridescent macroporous copolymer membranes with striking diffractive colors and much smoother surface ($R_q$~7.7±1.3 nm) resulted when the macroporous SMP samples dried out of ethanol instead of water. Second, our experiments showed that SMP membranes templated from large silica microspheres (>600 nm) maintained the ordered structure even when dried out of water.

TABLE 2.1

Roughness of 10 × 10 μm² AFM scan area of SMP sample surface.

| Samples | 3-D Areal Roughness | | Linear Profile Roughness | |
|---|---|---|---|---|
| | AA Roughness, $S_a$ [nm] | RMS Roughness, $S_q$ [nm] | AA Roughness, $R_a$ [nm] | RMS Roughness, $R_q$ [nm] |
| Water-dried | 46.5 ± 7.1 | 59.4 ± 9.9 | 34.6 ± 6.3 | 41.7 ± 7.8 |
| Liquid ethanol-activated | 8.7 ± 2.5 | 11.9 ± 4.3 | 6.3 ± 1.2 | 7.7 ± 1.3 |
| Acetone vapor-activated | 10.2 ± 1.6 | 14.0 ± 2.6 | 7.2 ± 1.1 | 8.9 ± 1.2 |

We evaluated the Young's modulus of the macroporous SMP membranes by in-situ nanoindentation tests. Three forces (100 μN, 200 μN, and 300 μN) were chosen to compare E of different indentation forces/depths. FIG. 2.9 shows the results of macroporous ETPTA 20-co-PEGDA 600 (1:3 ratio) membranes with 300 nm macropores dried out of ethanol and water, respectively. Apparently, all samples have Young's modulus of ~30 MPa, and the water-dried films are slightly stiffer than the ethanol-dried ones. This is reasonable as more air was trapped in the ethanol-dried samples with 3-D ordered macropores compared with the collapsed pores of the water-dried membranes. Similar E values were obtained from macroporous copolymer samples with other oligomer volumetric ratios (from 1:1 to 1:6) and macropore sizes. By using the Young-Laplace equation, we estimated the capillary pressure generated by evaporating water from the copolymer macropores with 300 nm diameter to be ~1 MPa (i.e., ~10 atm), which is comparable with the Young's modulus of the macroporous SMP membranes. Similar capillary pressure-induced macropore collapse has been reported during drying of macroporous polymer (e.g., polysulfone) reverse osmosis membranes used for water purification.[72,73]

The autonomous evaporation-assisted "cold" programming exhibited by the macroporous SMP membranes is in sharp contrast to the common "hot" programming process used by traditional SMPs. Even more interesting, a translucent macroporous SMP copolymer membrane with collapsed macropores momentarily changed color from pale white to brilliant iridescence (FIG. 2.3A) when the sample was exposed to various organic vapors (e.g., acetone, methanol, and chloroform) at ambient conditions. The cross-sectional SEM image in FIG. 2.3B shows a SMP copolymer sample after exposing to an acetone vapor. The recovery of the 3-D highly ordered photonic crystal structure (permanent configuration) is evident. By averaging over 50 different spots on a few SEM images, the thickness of the macroporous layers of the water-dried and the acetone vapor-recovered SMP samples was estimated to be 1.95±0.13 μm and 5.75±0.06 μm, respectively. The nearly 3-fold expansion of the macroporous layer indicates the collapsed macropores popped up into ordered arrays when triggered by acetone vapor exposure. The AFM image and the depth profile in FIG. 3c-d illustrate that the acetone-recovered macroporous SMP membrane has a much smoother surface than the water-dried sample (FIG. 2.2C-D). Table 2.1 compares the surface roughness of a SMP membrane dried out water, ethanol, and acetone vapor. The acetone vapor-activated sample has a slightly rougher surface than the liquid ethanol-recovered one; while both samples are significantly smoother than the water-dried membrane.

The instantaneous transition between a disordered temporary configuration and a 3-D highly ordered permanent structure, which leads to an easily perceived color change from translucence to striking iridescence, can be quantitatively characterized by measuring the normal-incidence reflection spectra using an optical spectrometer. FIG. 2.4 compares the optical reflection spectra obtained from a water-dried SMP membrane with 280 nm macropores (black line), and the same sample after exposed to acetone vapor (red line) and liquid ethanol (blue line). No apparent Bragg diffraction peaks are shown in the spectrum of the water-dried sample; while distinct diffraction peaks with well-defined Fabry-Perot fringes are present in the spectra of the samples triggered by acetone vapor and liquid ethanol, confirming the high crystalline quality of the recovered macroporous photonic crystals.[69] Additionally, the experimental spectrum of the ethanol-recovered sample matches well with the calculated spectrum using a scalar-wave approximation model, which assumes a perfect crystalline lattice.[74] We can then use the ethanol-activated SMP membrane as a fully recovered control to evaluate the completeness of macropore recovery under different triggering conditions. As shown in FIG. 2.4, the amplitude of the PBG peaks of the acetone vapor-activated sample is slightly lower than that of the liquid ethanol-recovered one. As the PBG optical density of a macroporous photonic crystal is a sensitive function of its crystalline thickness,[74] the smaller reflection amplitude indicates the acetone vapor-triggered macropore recovery is not as complete as the liquid ethanol-induced recovery. This agrees with the surface roughness results shown in Table 2.1.

Above we have shown that the chromogenic responses enabled by the macroporous SMP photonic crystals with micrometer-scale thickness provide a simple yet sensitive optical methodology for characterizing microscopic SM effects. We then used this optical tool to evaluate the reversibility, durability, and reproducibility of the vapor-triggered SMP membranes. FIGS. 2.5A and 2.5B compare the optical reflection spectra obtained from the same macroporous ETPTA 20-co-PEGDA 600 (1:3 ratio) membrane cyclically exposed to acetone vapor and then dried out of water for 10 times. The good reversibility and reproducibility of the sample are evident from the spectra and the comparison of the absolute reflection amplitude at 500 nm wavelength for the sample cyclically exposed to acetone vapor and water in FIG. 2.5C. Indeed, our extensive tests showed that the macroporous SMP copolymer membranes could be reused for over 500 times without any apparent degradation in the chromogenic response to acetone vapor.

We speculated that the capillary condensation and evaporation of fluids with low surface tension in macroporous SMP membranes played a critical role in the vapor-triggered SM recovery.[71, 75, 76] As shown by FIG. 2.6A-C, the translucent SMP membrane instantaneously changed color to reddish when the sample was close to the surface of liquid acetone, where the partial pressure of acetone vapor was high. Interestingly, the sample could become nearly transparent when it stayed close to the liquid acetone surface for a while. This indicates all macropores were filled up with condensed acetone whose refractive index ($n_{acetone} \sim 1.359$) is close to that of the ETPTA 20-co-PEGDA 600 copolymer ($n_{copolym} \sim 1.470$). The reddish color changed to greenish when the membrane moved away from the liquid acetone surface, and this red-green color transition was reversible. To gain quantitative insights into the capillary condensation of condensable vapors in the macroporous SMP membranes, we measured the normal-incidence optical reflection spectra for a sample with 300 nm macropores exposed to acetone vapors with different partial pressures (FIG. 2.6D). The diffraction peak red-shifts with increasing vapor pressure, and it nearly disappears (due to refractive index matching) when the vapor partial pressure is very high (682.8 mmHg). We can calculate the effective refractive index ($n_{eff}$) of the macroporous photonic crystals with condensed liquid using the Bragg diffraction equation: $\lambda = 2 \times n_{eff} \times d \times \sin\theta$, where d is the inter-plane distance and $\theta$ is $\pi/2$ for normal incidence. By assuming the macropores are close-packed and the volume fraction of air ($VF_{air}$) in a dry macroporous SMP membrane is 0.74, we can then calculate the volume fraction of the condensed acetone ($VF_{acetone}$) using $n_{eff} = n_{copolym} \times 0.26 + n_{air} \times (0.74 - VF_{acetone}) + n_{acetone} \times VF_{acetone}$, where $n_{copolym}$, $n_{air}$ and $n_{acetone}$ is 1.47, 1.0, and 1.359, respectively. As shown in previous work,[75-77] the condensed liquid forms a uniform thin layer on the walls of the macropores. The thickness of this liquid layer and the size of the remaining air cavities can be easily evaluated by using $VF_{acetone}$. The calculated radius of air cavities for the 5 samples with apparent diffraction peaks and increasing vapor pressures in FIG. 2.6D is 111.3, 99.8, 91.3, 81.9, sand 69.7 nm, respectively. We finally compared our experimental results with the predictions using the Kelvin equation, $$\ln \frac{P}{P_0} = \frac{2\gamma V_l}{rRT},$$

where P and $P_0$ are actual and saturation vapor pressure, $\gamma$ is the liquid/vapor surface tension, $V_l$ is the liquid molar volume, r is the radius of curvature.[75] The Kelvin equation has been widely utilized in describing the phenomenon of capillary condensation due to the presence of a curved meniscus. It predicts lnP is linearly proportional to 1/r when other variables are constant. Our experimental results match well with this prediction (inset of FIG. 2.6D).

In addition to the above capillary condensation and evaporation of fluids in macropores, the crystallinity of the SMP copolymers and the interactions between the polymer and various solvents could also significantly affect the SM recovery. It is well-known that polyethylene glycol which is a major component of ETPTA 20 and PEGDA 600 oligomers (see FIGS. 2.7A-B) can crystallize and the crystallinity can greatly impact the polymer properties, such as modulus, stiffness, and melting point. However, the DSC plots in FIG. 2.8 indicate the copolymers dried out of water, ethanol, and acetone are all amorphous at room temperature. FIGS. 2.10A-C show water drop profiles on ETPTA 20-co-PEGDA 600 (1:3 ratio) SMP membranes. 2.10A is bulk membrane with flat surface. 2.10B is a macroporous membrane with collapsed 280 nm macropores (dried out water). 2.10C is macroporous membrane with open macropores recovered by acetone vapor exposure. The effects of the polymer-solvent interactions on the wettability of the SMP copolymers were evaluated by measuring the apparent water contact angles (CAs) of macroporous membranes dried out of different solvents. FIGS. 2.11A-B show the typical water drop profiles on a bulk SMP membrane with flat surface, a macroporous film with collapsed macropores, and an acetone vapor-recovered macroporous membrane with ordered macropores. The apparent water CA averaged over 10 different spots for the above samples is 52.0±3.3°, 47.8±2.5°, and 40.0±3.2°, respectively, indicating the SMP copolymers are hydrophilic. The decrease in CAs for the macroporous membranes with collapsed and open macropores can be explained by the well-established Wenzel's wetting model, which predicts the CA will decrease with increasing porosity for hydrophilic materials. Solvent-induced polymer swelling can also significantly affect the macropore recovery process by expanding the intermolecular distance and by reducing macromolecular interactions. The swelling ratio, which is defined as $$\frac{W_{wet} - W_{dry}}{W_{dry}},$$

where $W_{wet}$ and $W_{dry}$ are the weights of the copolymer membrane after and prior to immersing in the solvent, can then be calculated. FIG. 2.12A-C shows the equilibrium swelling ratio of macroporous ETPTA 20-co-PEGDA 600 copolymer (1:3 ratio) is ≈0.5, ≈0.25, and ≈0.25 for water, ethanol, and acetone, respectively. These high swelling ratios are reasonable considering the hydrophilicity of the copolymers and the high content of polyethylene glycol functional groups in the macromolecules.

The overall shape memory cycle enabled by the novel vapor-responsive SMPs can be summarized as follows. When photopolymerized in the presence of the silica colloidal crystal template, the cross-linked polymer chains are in stress-free configurations which are energetically favorable. The large capillary pressure induced by the evaporation of water trapped in the templated macropores squeezes the 3-D ordered macropores into temporary disordered arrays. Excess stresses are stored in the deformed polymer chains and they tend to recover back to the original stress-free state due to entropy elasticity. The rapid capillary condensation of acetone vapors in the macropores triggers the instantaneous recovery of the permanent photonic crystal structure. As the surface tensions of the condensed liquids (e.g., acetone and methanol) are significantly lower than that of water, the evaporation-induced capillary pressure is not sufficient to deform the recovered macropores during capillary evaporation of the condensed liquids.

In conclusion, we have discovered a new type of vapor-responsive SMP that enables room-temperature operations for the entire shape memory cycle. The recovery of the permanent macroporous photonic crystal structure can be momentarily triggered by a variety of organic vapors. The striking chromogenic effect (from colorless to iridescent) induced by the disorder-order transition differs greatly from the typical color change with limited wavelength shift exhibited by traditional tunable photonic crystals. In addition, the thin photonic crystal structure provides a simple yet sensitive optical technique for investigating the intriguing SM effects at nanoscale. These smart stimuli-responsive materials could find important technological applications ranging from reconfigurable nanooptical devices to reusable chromogenic vapor sensors.

EXPERIMENTAL SECTION

Fabrication of macroporous SMP photonic crystal membranes: The synthesis of monodispersed silica microspheres with less than 5% diameter variation was performed by following the well-established Stober method.[78] The synthesized silica microspheres were purified in 200-proof ethanol by multiple (at least 6 times) centrifugation and redispersion cycles. The purified silica particles were then assembled into 3-D highly ordered colloidal crystals on glass microslides using the convective self-assembly technology.[70] The microslide with the silica colloidal crystal on its surface was covered by another microslide, separated by a double-sided adhesive tape spacer (~1.7 mm thick). By utilizing capillary force, the interstitials in-between the assembled silica microspheres were filled up with viscous oligomer mixtures consisting of ethoxylated (20) trimethylolpropane triacrylate (SR415, Sartomer) and polyethylene glycol (600) diacrylate (SR610, Sartomer) oligomers with varying volumetric ratios from 1:1 to 1:6. Darocur 1173 (2-hydroxy-2-methyl-1-phenyl-1-propanone, BASF, 1 wt %) was added as photoinitiator. The monomer mixture was photopolymerized by using a pulsed UV curing system (RC 742, Xenon) for 4 s. The solidified film was soaked in a 1 vol % hydrofluoric acid aqueous solution for 4 h and finally rinsed with deionized water.

Responses of Macroporous SMP Membranes Exposed to Acetone Vapors with Different Partial Pressures:

The templated macroporous SMP photonic crystal membrane was placed horizontally in a home-made environmental chamber.[77] A reflection probe (R600-7, Ocean Optics) connected to an Ocean Optics HR4000 high-resolution vis-NIR spectrometer was sealed in the environmental chamber to measure the optical reflectance from the SMP photonic crystal. The chamber was first purged with pure nitrogen gas for 2 min. It was then filled up with acetone vapors with different pressures. Dry nitrogen was used to control the total pressure of the chamber to 1 atm.

Sample Characterization:

SEM imaging was carried out on a FEI XL-40 FEG-SEM. A 15 nm thick gold layer was sputtered onto the samples prior to imaging. Amplitude-modulation atomic force microscopy (AM-AFM) was performed using a MFP-3D AFM (Asylum Research, Inc.) with a Nanosensor PPP-NCHR probe (tip radius<10 nm). Differential scanning calorimetric measurements were performed from −80 to 100° C. at a heating rate of 10° C. min$^{-1}$ using a TA Instruments DSC Q1000 and an empty pan as reference. The weight of specimens was 5.11-5.64 mg. Normal-incidence optical reflection spectra were obtained using the Ocean Optics HR4000 high-resolution vis-NIR spectrometer with the R600-7 reflection probe and a tungsten halogen light source (LS-1). Absolute reflectivity was obtained as the ratio of the sample spectrum and a reference spectrum, which was the optical density obtained from an aluminum-sputtered (1000 nm thick) silicon wafer. The apparent water contact angle was measured using a goniometer (NRL C.A. Goniometer, Ramé-Hart Inc.) with autopipetting and imaging systems. Thermogravimetric analysis (TGA) was carried out in air with a Perkin-Elmer Thermo Gravimetric Analyzer and a platinum crucible between 25° C. and 300° C. at a heating rate of 3° C./min. The swelling ratios of the macroporous SMP copolymer membranes in various solvents (water, ethanol, and acetone) were evaluated by measuring the masses of the membranes immersed in the solvents after different durations.

Nanoindentation Tests:

Nanoindentation tests were performed with a MFP-3D Nanoindenter (Asylum Research, Inc.) using a spherical sapphire indenter (tip radius ~125 μm). Such configuration of the instrument has a force and displacement resolution less than 3 μN and 1 nm, respectively. Due to the comparatively large contact area of the spherical tip, there is no need to perform a contact area calibration. A force controlled trapezoidal load function with a 5-2-2 seconds segments corresponding to loading-hold-unloading times was applied to all indentations. Three forces, 100 μN, 200 μN, and 300 μN, were chosen to compare the Young's modulus of different indentation forces/depths. With each force, ten impressions were indented on each sample with an interdistance of 200 μm, which is about ten times over the average residual impression size. All indentations were triggered by 7.5 μN force, corresponding to ~2 nm deflection in the indenter spring. Overall, 30 indents were made on each sample. All indents were made at room temperature (23° C.) and the system was allowed to reach thermal equilibrium for 30 minutes to minimize the thermal drift effect.

Scalar Wave Approximation Modeling:

The scalar wave theory developed for periodic dielectric structures, which solves Maxwell's equations by neglecting diffraction from all but one set of crystalline planes (e.g., the (111) planes in this study),[74] was utilized to calculate the normal-incidence optical reflection spectra from macroporous SMP photonic crystals. The structural parameters of the photonic crystals used in the optical modeling, including the size of the macropores and the crystalline thickness, were derived from SEM images. The refractive index of the SMP copolymers was assumed to be 1.47.

REFERENCES FOR EXAMPLE 2

[1] A. Lendlein, Ed. Shape Memory Polymers, Springer, New York, N.Y. 2010.
[2] W. M. Huang, B. Yang, Y. Q. Fu, Polyurethane Shape Memory Polymers, CRC Press, Boca Raton, Fla. 2012.
[3] D. Habault, H. Zhang, Y. Zhao, Chem. Soc. Rev. 2013, 42, 7244.
[4] C. Yakacki, K. Gall, Adv. Polym. Sci. 2010, 226, 147.
[5] T. Xie, Polymer 2011, 52, 4985.
[6] A. Lendlein, S. Kelch, Angew. Chem. Int. Ed. 2002, 41, 2034.
[7] C. Liu, H. Qin, P. T. Mather, J. Mater. Chem. 2007, 17, 1543.
[8] H. Meng, J. Hu, J. Intel. Mater. Syst. Str. 2010, 21, 859.
[9] T. D. Nguyen, C. M. Yakacki, P. D. Brahmbhatt, M. L. Chambers, Adv. Mater. 2010, 22, 3411.
[10] M. A. C. Stuart, W. T. S. Huck, J. Genzer, M. Mueller, C. Ober, M. Stamm, G. B. Sukhorukov, I. Szleifer, V. V. Tsukruk, M. Urban, F. Winnik, S. Zauscher, I. Luzinov, S. Minko, Nature Mater. 2010, 9, 101.
[11] C. M. Yakacki, Polym. Rev. 2013, 53, 1.
[12] C. J. Kloxin, C. N. Bowman, Chem. Soc. Rev. 2013, 42, 7161.
[13] M. Behl, M. Y. Razzaq, A. Lendlein, Adv. Mater. 2010, 22, 3388.
[14] L. Ionov, Polym. Rev. 2013, 53, 92.
[15] S. M. Felton, M. T. Tolley, B. Shin, C. D. Onal, E. D. Demaine, D. Rus, R. J. Wood, Soft Matter 2013, 9, 7688.
[16] A. Gugliuzza, E. Drioli, J. Membr. Sci. 2013, 446, 350.
[17] J. Leng, H. Lu, Y. Liu, W. M. Huang, S. Du, MRS Bull. 2009, 34, 848.
[18] M. F. Metzger, T. S. Wilson, D. Schumann, D. L. Matthews, D. J. Maitland, Biomed. Microdevices 2002, 4, 89.
[19] W. Small, T. S. Wilson, W. J. Benett, J. M. Loge, D. J. Maitland, Opt. Express 2005, 13, 8204.
[20] H. Tobushi, H. Hara, E. Yamada, S. Hayashi, Smart Mater. Struct. 1996, 5, 483.
[21] A. Lendlein, R. Langer, Science 2002, 296, 1673.
[22] L. Xue, S. Dai, Z. Li, J. Mater. Chem. 2012, 22, 7403.
[23] C. M. Yakacki, R. Shandas, C. Lanning, B. Rech, A. Eckstein, K. Gall, Biomaterials 2007, 28, 2255.
[24] D. J. Maitland, M. F. Metzger, D. Schumann, A. Lee, T. S. Wilson, Laser Surg. Med. 2002, 30, 1
[25] J. Leng, H. Lv, Y. Liu, S. Du, J. Appl. Phys. 2008, 104, 104917.
[26] H. Koerner, G. Price, N. A. Pearce, M. Alexander, R. A. Vaia, Nature Mater. 2004, 3, 115.
[27] C. S. Hazelton, S. C. Arzberger, M. S. Lake, N. A. Munshi, J. Adv. Mater. 2007, 39, 35.
[28] H. Meng, H. Mohamadian, M. Stubblefield, D. Jerro, S. Ibekwe, S.-S. Pang, G. Li, Smart Mater. Struct. 2013, 22.
[29] P. T. Mather, X. Luo, I. A. Rousseau, Annu. Rev. Mater. Res., Vol. 39, 2009, 445.
[30] B. Heuwers, A. Beckel, A. Krieger, F. Katzenberg, J. C. Tiller, Macromol. Chem. Phys. 2013, 214, 912.
[31] B. Heuwers, D. Quitmann, R. Hoeher, F. M. Reinders, S. Tiemeyer, C. Sternemann, M. Tolan, F. Katzenberg, J. C. Tiller, Macromol. Chem. Phys. 2013, 34, 180.
[32] T. Xie, X. Xiao, J. Li, R. Wang, Adv. Mater. 2010, 22, 4390.
[33] H. Xu, C. Yu, S. Wang, V. Malyarchuk, T. Xie, J. A. Rogers, Adv. Funct. Mater. 2013, 23, 3299.
[34] J. Kunzelman, T. Chung, P. T. Mather, C. Weder, J. Mater. Chem. 2008, 18, 1082.
[35] H. Lv, J. Leng, Y. Liu, S. Du, Adv. Eng. Mater. 2008, 10, 592.
[36] W. M. Huang, B. Yang, L. An, C. Li, Y. S. Chan, Appl. Phys. Lett. 2005, 86, 114105.
[37] H. Du, J. Zhang, Soft Matter 2010, 6, 3370.
[38] X. Gu, P. T. Mather, RSC Adv. 2013, 3, 15783.
[39] D. Quitmann, N. Gushterov, G. Sadowski, F. Katzenberg, J. C. Tiller, Adv. Mater. 2014, 26, 3441.
[40] X. M. Ding, J. L. Hu, X. M. Tao, C. P. Hu, G. Y. Wang, J. Appl. Polym. Sci. 2008, 107, 4061.
[41] J. D. Joannopoulos, R. D. Meade, J. N. Winn, Photonic Crystals: Molding the Flow of Light, Princeton University Press, Princeton 1995.
[42] C. Fenzl, T. Hirsch, 0. S. Wolfbeis, Angew. Chem. Int. Ed. 2015, 53, 3318.

[43] B. Hatton, L. Mishchenko, S. Davis, K. H. Sandhage, J. Aizenberg, Proc. Natl. Acad. Sci. USA 2010, 107, 10354.
[44] Y. A. Vlasov, X. Z. Bo, J. C. Sturm, D. J. Norris, Nature 2001, 414, 289.
[45] J. M. Weissman, H. B. Sunkara, A. S. Tse, S. A. Asher, Science 1996, 274, 959.
[46] A. C. Arsenault, T. J. Clark, G. Von Freymann, L. Cademartiri, R. Sapienza, J. Bertolotti, E. Vekris, S. Wong, V. Kitaev, I. Manners, R. Z. Wang, S. John, D. Wiersma, G. A. Ozin, Nature Mater. 2006, 5, 179.
[47] C. I. Aguirre, E. Reguera, A. Stein, Adv. Funct. Mater. 2010, 20, 2565.
[48] Y. Kang, J. J. Walish, T. Gorishnyy, E. L. Thomas, Nature Mater. 2007, 6, 957.
[49] H. Fudouzi, Y. N. Xia, Langmuir 2003, 19, 9653.
[50] J. Ge, J. Goebl, L. He, Z. Lu, Y. Yin, Adv. Mater. 2009, 21, 4259.
[51] J.-H. Jang, C. Y. Koh, K. Bertoldi, M. C. Boyce, E. L. Thomas, Nano Lett. 2009, 9, 2113.
[52] Y. Takeoka, M. Watanabe, Langmuir 2002, 18, 5977.
[53] J. Ge, Y. Hu, Y. Yin, Angew. Chem. Int. Ed. 2007, 46, 7428.
[54] E. P. Chan, J. J. Walish, A. M. Urbas, E. L. Thomas, Adv. Mater. 2013, 25, 3934.
[55] Z. Pan, J. Ma, J. Yan, M. Zhou, J. Gao, J. Mater. Chem. 2012, 22, 2018.
[56] I. B. Burgess, M. Loncar, J. Aizenberg, J. Mater. Chem. C 2013, 1, 6075.
[57] Y. Yue, T. Kurokawa, M. A. Hague, T. Nakajima, T. Nonoyama, X. Li, I. Kajiwara, J. P. Gong, Nature Commun. 2014, 5.
[58] Y. F. Yue, M. A. Hague, T. Kurokawa, T. Nakajima, J. P. Gong, Adv. Mater. 2013, 25, 3106.
[59] J. Cui, W. Zhu, N. Gao, J. Li, H. Yang, Y. Jiang, P. Seidel, B. J. Ravoo, G. Li, Angew. Chem. Int. Ed. 2014, 53, 3844.
[60] M. G. Han, C. G. Shin, S.-J. Jeon, H. Shim, C.-J. Heo, H. Jin, J. W. Kim, S. Lee, Adv. Mater. 2012, 24, 6438.
[61] D. Yang, S. Ye, J. Ge, Adv. Funct. Mater. 2014, 24, 3197.
[62] S. Ye, Q. Fu, J. Ge, Adv. Funct. Mater. 2014, 24, 6430.
[63] S. A. Asher, V. L. Alexeev, A. V. Goponenko, A. C. Sharma, I. K. Lednev, C. S. Wilcox, D. N. Finegold, J. Am. Chem. Soc. 2003, 125, 3322.
[64] J. H. Holtz, S. A. Asher, Nature 1997, 389, 829.
[65] C. G. Schaefer, M. Gallei, J. T. Zahn, J. Engelhardt, G. P. Hellmann, M. Rehahn, Chem. Mater. 2013, 25, 2309.
[66] C. G. Schaefer, D. A. Smolin, G. P. Hellmann, M. Gallei, Langmuir 2013, 29, 11275.
[67] Y. Fang, Y. L. Ni, S. Y. Leo, C. Taylor, V. Basile, P. Jiang, Nature Commun. 2015, under revision.
[68] O. D. Velev, T. A. Jede, R. F. Lobo, A. M. Lenhoff, Nature 1997, 389, 447.
[69] P. Jiang, K. S. Hwang, D. M. Mittleman, J. F. Bertone, V. L. Colvin, J. Am. Chem. Soc. 1999, 121, 11630.
[70] P. Jiang, J. F. Bertone, K. S. Hwang, V. L. Colvin, Chem. Mater. 1999, 11, 2132.
[71] S. J. Gregg, K. S. W. Sing, Adsorption, Surface Area and Porosity, Academic Press Inc., London 1982.
[72] J. T. Tsai, Y. S. Su, D. M. Wang, J. L. Kuo, J. Y. Lai, A. Deratani, J. Membr. Sci. 2010, 362, 360.
[73] M. D. Mason, D. J. Sirbuly, S. K. Buratto, Thin Solid Films 2002, 406, 151.
[74] J. F. Bertone, P. Jiang, K. S. Hwang, D. M. Mittleman, V. L. Colvin, Phys. Rev. Lett. 1999, 83, 300.
[75] Z. Gemici, P. I. Schwachulla, E. H. Williamson, M. F. Rubner, R. E. Cohen, Nano Lett. 2009, 9, 1064.
[76] R. A. Potyrailo, H. Ghiradella, A. Vertiatchikh, K. Dovidenko, J. R. Cournoyer, E. Olson, Nature Photon. 2007, 1, 123.
[77] H. T. Yang, P. Jiang, Appl. Phys. Lett. 2011, 98, 011104.
[78] W. Stober, A. Fink, E. Bohn, J. Colloid Interf. Sci. 1968, 26, 62.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A structure comprising:
a macroporous photonic crystal membrane including a three dimensional array of macropores, wherein a three dimensional polymer framework separates the macropores, wherein the polymer framework is made of a copolymer of two oligomers, wherein the two oligomers are ethoxylated (20) trimethylolpropane triacrylate (ETPTA 20) and polyethylene glycol (600) diacrylate (PEGDA 600), wherein when the macropores are in a collapsed state, the macroporous photonic crystal membrane is substantially transparent and wherein when the macropores are in an uncollapsed state, the macroporous photonic crystal membrane has an iridescent color.

2. The structure of claim 1, wherein the three dimensional ordered array of macropores has a thickness of about 1 micron to 300 microns.

3. The structure of claim 1, wherein macropores have a diameter of about 100 nm to 600 nm.

4. The structure of claim 1, wherein the copolymer has a glass transition temperature of about −40° C. to −42° C.

5. The structure of claim 1, wherein the macroporous photonic crystal membrane has the characteristic of when exposed to a liquid, the uncollapsed macropores transform to their collapsed state.

6. The structure of claim 1, wherein the macroporous photonic crystal membrane has the characteristic of when the macropores are exposed to a vapor, the macropores transform into an uncollapsed state.

7. The structure of claim 6, wherein the vapor is selected from the group consisting of: acetone, methanol, dichloromethane, benezene, toluene, and ethanol.

8. The structure of claim 6, wherein the iridescent color is caused by Bragg diffraction of visible light and exposure to different gas vapors results in distinguishable and different Bragg diffraction of visible light.

9. The structure of claim 1, wherein the macroporous photonic crystal membrane has the characteristic of when exposed to a liquid, the uncollapsed macropores transform to their collapsed state, wherein the macroporous photonic crystal membrane has the characteristic of when the macropores are exposed to a vapor, the macropores transform into an uncollapsed state.

10. A method of making a structure, comprising:
disposing nanoparticles onto a surface to form a three dimensional array of particles;
introducing a prepolymer mixture to the array of particles;
polymerizing the prepolymer mixture to form a polymer framework around the three dimensional array of particles; and
removing the particles to form a three dimensional array of macropores in a macroporous photonic crystal membrane, wherein the three dimensional polymer framework separates the macropores, wherein the polymer framework is made of a copolymer of two oligomers, wherein the two oligomers are ethoxylated (20) trimethylolpropane triacrylate (ETPTA 20) and polyethylene glycol (600) diacrylate (PEGDA 600), wherein when the macropores are in a collapsed state the macroporous photonic crystal membrane is substantially transparent, wherein when the macropores are in an uncollapsed state the macroporous photonic crystal membrane has an iridescent color.

11. The method of claim 10, wherein the particles are silica particles.

12. The method of claim 10, wherein removing includes dissolving the particles.

13. The method of claim 10, further comprising: drying the macroporous photonic crystal membrane, wherein the macropores collapse so that the macroporous photonic crystal membrane is substantially transparent.

14. The method of claim 10, wherein the copolymer has a glass transition temperature of about −40° C. to −42° C.

* * * * *